(12) United States Patent
Cuero Rengifo

(10) Patent No.: US 11,603,549 B2
(45) Date of Patent: Mar. 14, 2023

(54) BIOLOGICAL DEVICES AND METHODS OF USE THEREOF TO PRODUCE CAROTENOIDS

(71) Applicant: Bio Capital Holdings, LLC, Houston, TX (US)

(72) Inventor: Raul Cuero Rengifo, Cypress, TX (US)

(73) Assignee: Bio Capital Holdings, LLC, Houston, TX (US)

( * ) Notice: Subject to any disclaimer, the term of this patent is extended or adjusted under 35 U.S.C. 154(b) by 258 days.

(21) Appl. No.: 16/646,216

(22) PCT Filed: Sep. 10, 2018

(86) PCT No.: PCT/US2018/050144
§ 371 (c)(1),
(2) Date: Mar. 11, 2020

(87) PCT Pub. No.: WO2019/055326
PCT Pub. Date: Mar. 21, 2019

(65) Prior Publication Data
US 2020/0270667 A1   Aug. 27, 2020

Related U.S. Application Data

(60) Provisional application No. 62/557,214, filed on Sep. 12, 2017.

(51) Int. Cl.
| | |
|---|---|
| *C12P 23/00* | (2006.01) |
| *C12N 9/02* | (2006.01) |
| *C12N 9/10* | (2006.01) |
| *C12N 9/90* | (2006.01) |
| *C12N 15/52* | (2006.01) |
| *C12N 15/63* | (2006.01) |

(52) U.S. Cl.
CPC ............ *C12P 23/00* (2013.01); *C12N 9/0073* (2013.01); *C12N 9/1022* (2013.01); *C12N 9/90* (2013.01); *C12N 15/52* (2013.01); *C12N 15/63* (2013.01); *C12Y 114/13129* (2013.01); *C12Y 202/01007* (2013.01); *C12Y 505/01018* (2013.01)

(58) Field of Classification Search
CPC ..... C12P 23/00; C12N 9/0073; C12N 9/1022; C12N 9/90; C12N 15/52; C12N 15/63; C12N 9/0077; C12Y 114/13129; C12Y 202/01007; C12Y 505/01018
See application file for complete search history.

(56) References Cited

U.S. PATENT DOCUMENTS

| | | |
|---|---|---|
| 8,288,149 B2 | 10/2012 | Bailey et al. |
| 2008/0124755 A1 | 5/2008 | Louie et al. |
| 2009/0094707 A1 | 4/2009 | Cirpus et al. |
| 2013/0338348 A1 | 12/2013 | Rommens et al. |
| 2014/0123339 A1 | 5/2014 | Albertsen et al. |
| 2016/0017362 A1 | 1/2016 | Cuero Rengifo et al. |
| 2016/0168214 A1 | 6/2016 | Cuero Rengifo et al. |

FOREIGN PATENT DOCUMENTS

| | | |
|---|---|---|
| EP | 2371967 A1 | 10/2011 |
| WO | 2014140924 A2 | 9/2014 |

OTHER PUBLICATIONS

Whisstock et al. Quaterly Reviews of Biophysics, 2003, "Prediction of protein function from protein sequence and structure", 36(3):307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
Carquet et al. Transcriptional interference and ORF nature strongly affect promoter strength in a reconstituted metabolic pathway. Frontiers in Bioengineering and Biotechnology (2015), 3: 1-9.*
Keasling, Synthetic biology and the development of tools for metabolic engineering, Metabolic Engineering 14 (2012) 189-195.
Matthews et al., Metabolic engineering of carotenoid accumulation in *Escherichia coli* by modulation of the isoprenoid precursor pool with expression of deoxyxylulose phosphate synthase, Appl Microbiol Biotechnol (2000) 53: 396-400.
International Search Report and Written Opinion issued for PCT/IB2014/001232, dated Nov. 6, 2014.
Asaph et al., Volatile science? Metabolic engineering of terpenoids in plants, Trends in Plant Science, vol. 10, No. 12, p. 594-602, 2005.
Arrach et al., A single gene for lycopene cyclase, phytoene synthase, and regulation of carotene biosynthesis in Phycomyces, PNAS, vol. 98, No. 4, p. 1687-1692, 2001.
Cazzonelli et al., Source to sink: regulation of carotenoid biosynthesis in plants, Trends in Plant Science vol. 15 No. 5, p. 266-274, 2010.
Cunningham et al., Functional Analysis of the B and ε Lycopene Cyclase Enzymes of Arabidopsis Reveals a Mechanism for Control of Cyclic Carotenoid Formation, The Plant Cell, vol. 8, 1613-1626, 1996.
International Search Report and Written Opinion issued for PCT/US2018/050144, dated Jan. 25, 2019.

\* cited by examiner

*Primary Examiner* — Iqbal H Chowdhury
(74) *Attorney, Agent, or Firm* — Thomas | Horstemeyer, LLP

(57) ABSTRACT

Described herein are devices and methods for using the same to produce carotenoids. The carotenoids produced by the devices and methods disclosed herein do not require the ultra purification that is common in conventional or commercial methods. The devices and methods disclosed herein also enhance one or more physical properties of plants treated with the devices described herein.

30 Claims, 4 Drawing Sheets

Specification includes a Sequence Listing.

BIOLOGICAL DEVICES AND METHODS OF USE THEREOF TO PRODUCE CAROTENOIDS

CROSS REFERENCE TO RELATED APPLICATIONS

This application claims priority upon U.S. provisional application Ser. No. 62/557,214 filed on Sep. 12, 2017. This application is hereby incorporated by reference in its entirety.

CROSS REFERENCE TO SEQUENCE LISTING

The genetic components described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

Carotenoids are fat-soluble terpenoid pigments produced by plants, algae, some bacteria, and some fungi, and are found in egg yolks, autumn leaves of many deciduous tree species, and some crustacean shells that appear to be red, orange, or yellow in color due to absorption of visible light in the wavelength range of approximately 400-550 nm. The length of the polyene tail of a carotenoid molecule determines the specific wavelengths of light absorbed. All carotenoids are tetraterpene derivatives (i.e., are produced from 8 isoprene molecules). Many carotenoids can be converted to retinol and thus have vitamin A activity, and carotenoids can also act as antioxidants, protecting cells and organelles such as chloroplasts from UV-induced damage. A diet rich in foods containing carotenoid compounds has been shown to be protective against certain types of cancers including head and neck cancers, prostate cancer, and breast cancer. Carotenoid pigments, including lutein, meso-zeaxanthin, and zeaxanthin are present in the macula of the eye and have been shown to have therapeutic value for degenerative eye diseases, as well as to support the heart and overall cardiovascular health. Carotenoids are also found in skincare and cosmetic preparations, where they may help reduce the impact of environmental factors such as UV radiation that are associated with skin aging.

Common carotenoid pigments include xanthophylls such as lutein, zeaxanthin, violaxanthin, astaxanthin, caspanthin, fucoxanthin, and beta-cryptoxanthin, which contain oxygen atoms, as well as carotenes such as beta-carotene, alpha-carotene, gamma-carotene, delta-carotene, and lycopene, which are hydrocarbons. Although these compounds are available in some food crops, such as, for example, carrots, sweet potatoes, leafy greens (e.g., spinach, kale, mustard greens, dandelion greens, collard greens, turnip greens, and romaine lettuce), tomatoes, squash, broccoli, pumpkin, citrus fruits, corn (maize), bell peppers, avocado, peas, cantaloupe, and watermelons, it would be desirable to have a new method of producing carotenoids on an abbreviated time scale, to generate large quantities of these compounds to be added to food, pharmaceutical, and cosmetic preparations. The new method would, ideally, be inexpensive, would not result in the production of genetically-modified plants, would require fewer organic solvents for extraction than traditional methods for carotenoid extraction, and would result in higher carotenoid production using less biomass than traditional methods, thus not requiring agronomic practices and large growing fields.

SUMMARY

Described herein are devices and methods for using the same to produce carotenoids. The carotenoids produced by the devices and methods disclosed herein do not require the ultra purification that is common in conventional or commercial methods. The devices and methods disclosed herein also enhance one or more physical properties of plants treated with the devices described herein.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1A:
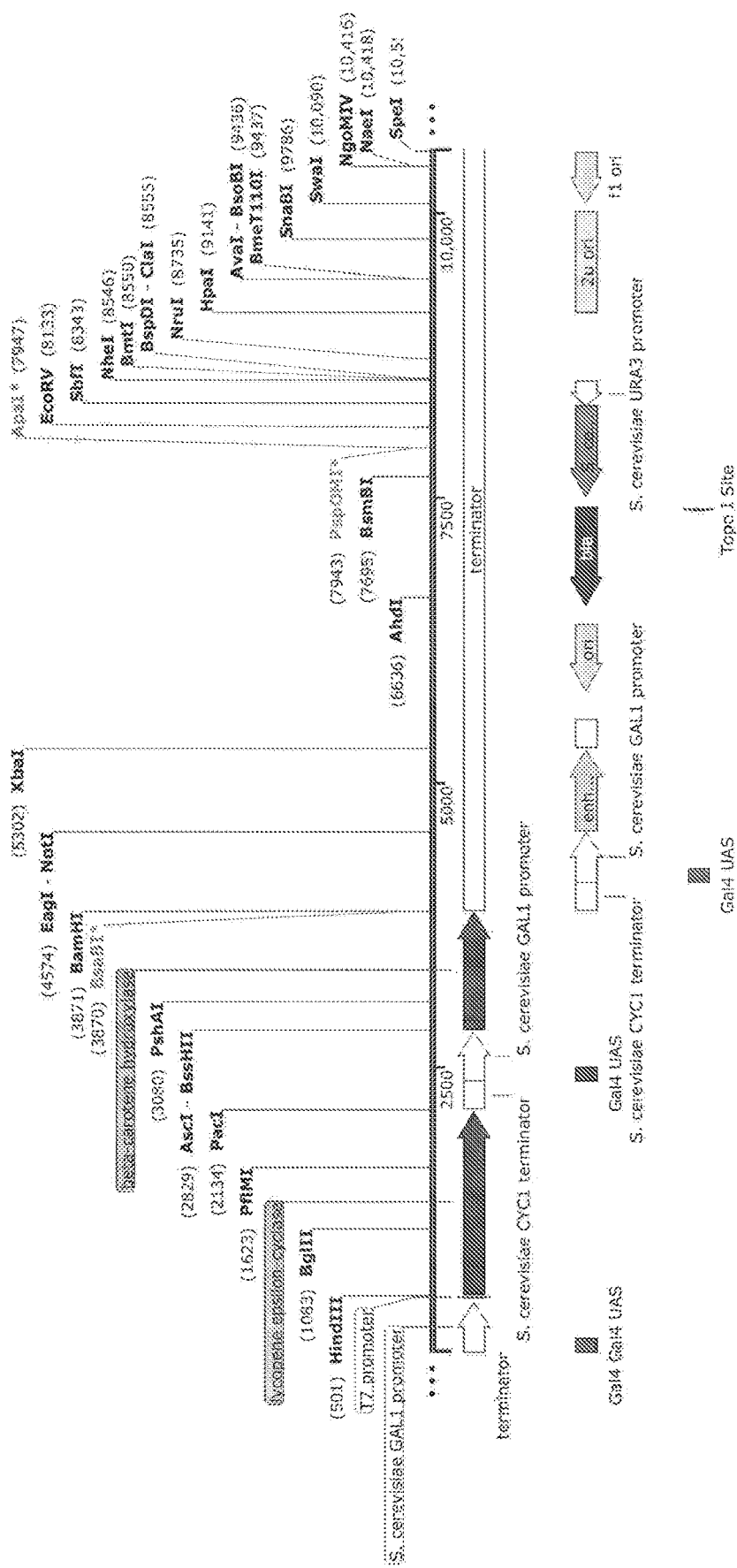
FIGS. 1A and 1B show, respectively, a linear and circular schematic of a constructed pYES2 plasmid showing the direction, placement, and size of genetic parts used of an exemplary DNA device described herein.

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "an isolated nucleic acid" includes mixtures of two or more such nucleic acids, and the like.

"Optional" or "optionally" means that the subsequently described event or circumstance can or cannot occur, and that the description includes instances where the event or circumstance occurs and instances where it does not. For example, the phrase "optionally includes a gene for a selective marker" means that the gene may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference of each various individual and collective combination and permutation of these compounds may not be explicitly disclosed, each is specifically contemplated and described herein. For example, if a bacterium is disclosed and discussed and a number of different compatible bacterial plasmids are discussed, each and every combination and permutation of bacterium and bacterial plasmid that is possible is specifically contemplated unless specifically indicated to the contrary. For example, if a class of molecules A, B, and C are disclosed as well as a class of molecules D, E, and F, and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if a variety of additional steps can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

"Heterologous" genes and proteins are genes and proteins that have been experimentally put into a cell that are not normally expressed by that cell. A heterologous gene may be cloned or derived from a different cell type or species than the recipient cell or organism. Heterologous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed for only a limited period of time).

"Competent cells" refers to microbial cells capable of taking up heterologous DNA. Competent cells can be purchased from a commercial source, or cells may be made competent using procedures known in the art.

I. DNA Constructs and Biological Devices

Described herein are devices and methods for using the same to produce carotenoids. The device is generally composed of host cells, where the host cells are transformed with a DNA construct described herein that promotes the expression of carotenoids. Examples of carotenoids include, but are not limited to, lycopene, lutein, zeaxanthin, violaxanthin, astaxanthin, caspanthin, fucoxanthin, beta-cryptoxanthin, beta-carotene, alpha-carotene, gamma-carotene, delta-carotene, epsilon-carotene, canthaxanthin, antheraxanthin, 7-8-didehydroastaxanthin, alpha-cryptoxanthin, zeta-carotene, diatoxanthin, lactucaxanthin, phytoene, neurosporene, rhodopin, fucoxanthinol, peridinin, siphonaxanthin, neoxanthin, spirilloxanthin, spheroidene, uriolide, uriolide acetate, spheroidenone, rhodopin glucoside, or a combination thereof.

It is understood that one way to define the variants and derivatives of the genetic components and DNA constructs described herein is through defining the variants and derivatives in terms of homology/identity to specific known sequences. Those of skill in the art readily understand how to determine the homology of two nucleic acids. For example, the homology can be calculated after aligning the two sequences so that the homology is at its highest level. Another way of calculating homology can be performed by carrying out published algorithms (see Zuker, M., *Science*, 1989, 244:48-52 or Jaeger et al., *Proc. Natl. Acad. Sci. USA*, 1989, 86:7706-7710 or Jaeger et al., *Methods Enzymol.*, 1989, 183:281-306, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of conservative mutations and homology can be combined together in any combination, such as embodiments that have at least 70%, 75%, 80%, 85%, 90%, 95%, or 99% homology to a particular sequence wherein the variants are conservative mutations. It is understood that any of the sequences described herein can be a variant or derivative having the homology values listed above.

In one aspect, a database such as, for example, GenBank, can be used to determine the sequence of genes and/or regulatory regions of interest, the species from which these elements originate, and related homologous sequences.

In one aspect, the DNA construct includes the following genetic components: (a) a gene that expresses beta-carotene hydroxylase, (b) a gene that expresses lycopene epsilon cyclase, and (c) a gene that expresses 1-deoxy-D-xylylose phosphate synthase.

In another aspect, the DNA construct includes the following genetic components: (a) a gene that expresses beta-carotene hydroxylase and (b) a gene that expresses lycopene epsilon cyclase, wherein at least one promoter positioned before the gene that expresses beta-carotene hydroxylase and the gene that expresses lycopene epsilon cyclase.

In one aspect, the gene that expresses DXP synthase is isolated from plants. In a further aspect, the plant is *Stevia rebaudiana*, chrysanthemum, castor bean, Russian dandelion, cassava, rubber tree, *Eucommia ulmoides, Jatropha curcas, Erhtyranthe guttata*, a wild or cultivated tobacco species, achiote, English walnut, sweet osmanthus, domestic apple, wild tomato, potato, or another plant. In one aspect, the gene that expresses DXP synthase has SEQ ID NO. 1 or a sequence having at least 70%, at least 80%, at least 90% homology therewith, or at least 95% homology therewith. In one aspect, the gene that expresses DXP synthase is isolated from *Arabidopsis thaliana* and can be found in GenBank with GI number AEE76516.1. In another aspect, GenBank accession numbers for useful DXP synthase genes can be found in Table 1.

TABLE 1

Examples of DXP Synthase Genes

| | | |
|---|---|---|
| FJ214107.1 | KR704421.1 | XM_019580622.1 |
| AJ429232.2 | KR704420.1 | XM_008451967.2 |
| KT276232.1 | EF043284.1 | XM_017045366.1 |
| AB205044.1 | XM_017392124.1 | XM_008451966.2 |
| KT899414.1 | NM_001345870.1 | XM_007156399.1 |
| XM_021774212.1 | XM_015203416.1 | KY502270.1 |
| XM_021811802.1 | XM_006353091.2 | XM_016898290.1 |
| DQ473433.1 | XM_011012876.1 | XM_019565830.1 |
| AB294699.1 | XM_006380518.1 | XM_018114317.1 |
| XM_002532338.2 | KM879186.1 | XM_016879435.1 |
| XM_021781018.1 | KF957679.1 | XM_020401672.1 |
| XM_021781017.1 | XM_008353503.2 | XM_020401671.1 |
| JX458818.2 | KF957703.1 | XM_006426184.1 |
| XM_012226308.2 | XM_008394543.2 | XM_004134220.2 |
| XM_012989649.1 | AJ011840.2 | XM_007156398.1 |
| XM_009592196.2 | XM_021946477.1 | XM_012581805.1 |
| XM_021776767.1 | XM_004289469.2 | XM_010115150.1 |
| XM_019406517.1 | XM_021946478.1 | KR132245.1 |
| KX400842.1 | XM_016898289.1 | AK339569.1 |
| XM_021776766.1 | XM_016034990.1 | XM_006466273.2 |
| KT358984.1 | XM_017779849.1 | KX387389.1 |
| XM_018954512.1 | XM_007207978.2 | XM_019568328.1 |
| XM_016592817.1 | XM_011101661.2 | KY014577.1 |
| XM_009769974.1 | XM_016879434.1 | XM_014650064.1 |
| NM_001325159.1 | XM_020361523.1 | XM_008812725.2 |
| JQ085430.1 | KF355950.1 | XM_013590619.1 |
| XM_008340252.2 | XM_016797343.1 | AJ430048.1 |
| XM_008340251.2 | XM_008238129.2 | AF443590.1 |
| KM974886.1 | XM_008238123.2 | XM_014650447.1 |
| AY687353.1 | XM_002266889.4 | XM_017572049.1 |
| XM_019327463.1 | XM_004509650.2 | XM_021139128.1 |
| XM_019327462.1 | XM_020384669.1 | XM_021119612.1 |
| XM_009365960.2 | XM_019589828.1 | XM_010935272.2 |
| XM_009366530.2 | | |

DXP synthase, or 1-deoxy-D-xylulose 5-phosphate synthase (sometimes abbreviated DOXP synthase of DXS) uses glycolytic pathway intermediates pyruvic acid and glyceraldehyde 3-phosphate to generate 1-deoxy-D-xylulose 5-phosphate. It is an enzyme on the non-mevalonate pathway (also known as the mevalonate-independent pathway), which is an alternative metabolic pathway for isoprenoid biosynthesis. In one aspect, DXP synthase expressed by a gene in the DNA constructs described herein catalyzes the formation of precursor molecules to carotenoids.

In one aspect, the carotenoids are produced herein using starting materials from the non-mevalonate pathway for isoprenoid biosynthesis. In an alternative aspect, the starting materials for carotenoid biosynthesis used herein are generated via the mevalonate pathway. In still another aspect, the starting materials for carotenoid biosynthesis are generated from both the mevalonate and non-mevalonate pathways.

In one aspect, the gene that expresses a carotenoid hydroxylase expresses beta-carotene hydroxylase and is isolated from plants. In another aspect, the gene that expresses beta-carotene hydroxylase is isolated from bacteria. In one aspect, the bacteria are cyanobacteria. In a further aspect, the cyanobacteria are *Synechococcus* sp. WH8102, *Synechococcus elongates* PCC6301 or PCC7942, or *Prochlorus marinus*. In a still further aspect, the *P. marinus* is subspecies *marinus*, strain CCMP1375. In a further aspect, the gene that expresses beta-carotene hydroxylase in the DNA construct has SEQ ID NO. 2 or a sequence having at least 70%, at least 80%, at least 90% homology therewith, or at least 95% homology therewith.

In another aspect, the gene that expresses a carotenoid hydroxylase expresses an epsilon ring carotenoid hydroxylase. In a further aspect, the gene that expresses the epsilon ring carotenoid hydroxylase is isolated from a plant. In one aspect, the plant is *Arabidopsis thaliana, Medicago truncatula*, carrot (*Daucus carota*), ginkgo (*Ginkgo biloba*), soybean (*Glycine max*), rice (*Oryza sativa*), corn (*Zea mays*), or potato (*Solanum tuberosum*). In a further aspect, the plant is a wild type plant. In an alternative aspect, the plant is a plant that has been subjected to site-directed mutagenesis or another mutagenesis technique.

In one aspect, the gene that expresses a carotenoid hydroxylase is isolated from *Synechococcus* sp. WH 8102 and can be found in GenBank with GI number CAE06806. In another aspect, GenBank accession numbers for useful carotenoid hydroxylase genes can be found in Table 2.

TABLE 2

Examples of Carotenoid Hydroxylase Genes

| | | |
|---|---|---|
| AAC44852 | ABC68396 | EAE78743 |
| AAC49443 | ABD28565 | EAF12173 |
| AAD54243 | BAA14129 | EAH29370 |
| AAG10430 | BAB79605 | EAH44202 |
| AAG10793 | BAC77670 | EAI00766 |
| AAG33636 | BAD07283 | EAI29017 |
| AAL80006 | BAD07291 | EAJ30844 |
| AAM44971 | BAD94136 | EAJ72524 |
| AAM51300 | CAA70427 | EAK10611 |
| AAM77007 | CAA70888 | EAK53455 |
| AAN85601 | CAB55625 | EAK63955 |
| AAO53295 | CAB55626 | H90469 |

TABLE 2-continued

Examples of Carotenoid Hydroxylase Genes

| | | |
|---|---|---|
| AAS48097 | CAB56060 | NP_190881 |
| AAS55552 | CAC06712 | NP_745389 |
| AAS88426 | CAC95130 | NP_922503 |
| AAT28222 | EAB30128 | NP_922604 |
| AAT48741 | EAC49462 | P54973 |
| AAT84408 | EAC86129 | Q44262 |
| AAV85452 | EAD61089 | S52982 |
| AAV85453 | EAD76156 | XP_473611 |
| ABB47954 | EAD88640 | YP_024309 |
| ABB52076 | EAE27903 | ZP_003055 |
| ABC59110 | EAE28203 | ZP_003107 |

In another aspect, the gene that expresses lycopene cyclase is a lycopene epsilon-cyclase. Further in this aspect, the lycopene epsilon-cyclase is isolated from plants. In a further aspect, the plant is corn (*Zea mays*), sorghum or milo (*Sorghum bicolor*), or *Arabidopsis thaliana*. In another aspect, the gene that expresses lycopene epsilon-cyclase is isolated from bacteria. In a further aspect, the bacteria are *Xanthobacter autotrophicus* PY2. In a further aspect, the gene that expresses lycopene epsilon-cyclase in the DNA construct has SEQ ID NO. 3 or a sequence having at least 70%, at least 80%, at least 90% homology, at least 95% homology therewith.

In another aspect, the gene that expresses lycopene cyclase is a single gene that expresses both phytoene synthase and lycopene cyclase. In still another aspect, the gene that expresses lycopene cyclase is a lycopene beta-cyclase. In yet another aspect, the gene that expresses lycopene cyclase is a single protein with separate beta and epsilon subunits.

In any of the above aspects, additional plants with useful lycopene cyclase genes include *Adonis palaestina*, carrot (*Daucus carota*), Mexican or Aztec marigold (*Tagetes erecta*), spinach (*Spinacia oleracea*), chrysanthemum (various species, subspecies, and crosses), rice (*Oryza sativa*), oranges (*Citrus sinensis*), pomelo (*Citrus maxima*), grapefruit (*Citrus ×paradisi*), potato (*Solanum tuberosum*), lemon (*Citrus limon*), satsuma (*Citrus ×unshiu*), bald cypress (*Taxodium distichum*), Japanese cedar (*Cryptomeria japonica*), achiote (*Bixa orellana*), millet (*Setaria italica*), bell pepper or chili pepper (*Capsicum annuum*), or tobacco (*Nicotiana tabacum*). In any of the above aspects, additional bacteria with useful lycopene cyclase genes include *Prochlorococcus* species, *Synechococcus* species, and *Deinococcus* species.

In one aspect, the gene that expresses lycopene cyclase is isolated from *Zea mays* (corn) and can be found in GenBank with GI number ABU93262. In another aspect, GenBank accession numbers for useful lycopene cyclase genes can be found in Table 3.

TABLE 3

Examples of Lycopene Cyclase Genes

| | | |
|---|---|---|
| 1613414C | BAE43548 | EAK24859 |
| A49558 | BAE43549 | EAK28345 |
| AAA19428 | BAE43550 | EAK34732 |
| AAA32836 | BAE43551 | EAK34736 |
| AAA64982 | BAE43552 | EAK37296 |
| AAA81880 | BAE43553 | EAK37521 |
| AAB53336 | BAE43554 | EAK50052 |
| AAB87738 | BAE43555 | EAK56335 |
| AAC44849 | BAE43556 | G84363 |
| AAD38049 | BAE43557 | NP_274195 |
| AAD38051 | BAE43558 | NP_284085 |

TABLE 3-continued

Examples of Lycopene Cyclase Genes

| | | |
|---|---|---|
| AAF23013 | BAE43559 | NP_294525 |
| AAF34191 | BAE43560 | NP_294586 |
| AAF44700 | BAE78471 | NP_388961 |
| AAF78202 | BAE79544 | NP_441168 |
| AAF82616 | BAE79549 | NP_443763 |
| AAG10427 | C90061 | NP_624523 |
| AAG10428 | CAA47625 | NP_630832 |
| AAG10429 | CAA54961 | NP_662273 |
| AAG21133 | CAA68575 | NP_682350 |
| AAG28701 | CAB07958 | NP_693381 |
| AAK07430 | CAB38740 | NP_786525 |
| AAK07431 | CAB51949 | NP_822199 |
| AAK07433 | CAB56063 | NP_822829 |
| AAK07434 | CAB86388 | NP_851527 |
| AAK07734 | CAB92977 | NP_868799 |
| AAK07735 | CAB93342 | NP_874560 |
| AAK15621 | CAB93661 | NP_875182 |
| AAL02001 | CAB94795 | NP_875528 |
| AAL47019 | CAC19567 | NP_879992 |
| AAL69394 | CAC27383 | NP_884101 |
| AAL76346 | CAD19988 | NP_889809 |
| AAL82578 | CAD29284 | NP_892264 |
| AAL92114 | CAD70565 | NP_892751 |
| AAL92175 | CAE76609 | NP_893181 |
| AAM14335 | E37802 | NP_894954 |
| AAM21152 | E84320 | NP_895600 |
| AAM45379 | EAA98758 | NP_895828 |
| AAM45381 | EAB01965 | NP_896821 |
| AAM45382 | EAB04170 | NP_898345 |
| AAM48647 | EAB07138 | NP_902648 |
| AAM62787 | EAB09791 | NP_902649 |
| AAM94363 | EAB19826 | NP_924690 |
| AAN85600 | EAB35029 | NP_931516 |
| AAN86060 | EAB41375 | NP_946861 |
| AAO18661 | EAB78706 | NP_949079 |
| AAO24767 | EAB92586 | NP_962005 |
| AAO39835 | EAC06949 | NP_968601 |
| AAO46895 | EAC18360 | O07333 |
| AAO47570 | EAC25793 | O65837 |
| AAO64977 | EAC29883 | P08196 |
| AAO73816 | EAC32813 | P21683 |
| AAP22038 | EAC33105 | P37269 |
| AAP55451 | EAC38486 | P37271 |
| AAP55453 | EAC52233 | P37272 |
| AAP55461 | EAC60029 | P53797 |
| AAP55471 | EAC68026 | P54975 |
| AAP55484 | EAC96197 | P54977 |
| AAP55486 | EAD08701 | P65860 |
| AAP56083 | EAD20866 | Q38932 |
| AAP56124 | EAD32755 | Q40424 |
| AAP56127 | EAD38008 | Q42435 |
| AAP56136 | EAD50152 | Q43415 |
| AAP56148 | EAD50402 | Q43503 |
| AAP56155 | EAD81123 | Q43578 |
| AAP56156 | EAD93882 | Q9SEA0 |
| AAP56157 | EAE12860 | Q9SSU8 |
| AAP56158 | EAE16121 | Q9UUQ6 |
| AAP79176 | EAE31084 | S22474 |
| AAQ02668 | EAE35665 | S32170 |
| AAQ91837 | EAE44717 | S52587 |
| AAR08445 | EAE46627 | S56668 |
| AAR31885 | EAE47846 | S66349 |
| AAR37803 | EAE72264 | S66350 |
| AAR37856 | EAE76009 | S68307 |
| AAR86104 | EAE86335 | T10702 |
| AAR87868 | EAE89581 | T46594 |
| AAR89632 | EAF18881 | T50746 |
| AAR98492 | EAF64277 | T50895 |
| AAS02284 | EAF67931 | XP_324765 |
| AAS17009 | EAF84745 | XP_383242 |
| AAS18307 | EAF94004 | XP_403902 |
| AAS48096 | EAG06083 | XP_463351 |
| AAT28184 | EAG21950 | XP_464409 |
| AAT35222 | EAG43625 | YP_006040 |
| AAT38473 | EAG50171 | YP_103126 |
| AAT46065 | EAG57517 | YP_112342 |
| AAT46069 | EAG62787 | YP_117945 |
| AAT74581 | EAG65580 | YP_120611 |

TABLE 3-continued

Examples of Lycopene Cyclase Genes

| | | |
|---|---|---|
| AAT76051 | EAG68110 | YP_136628 |
| AAT90319 | EAG72283 | YP_136629 |
| AAU05145 | EAG78750 | YP_145340 |
| AAU05146 | EAG80445 | YP_145343 |
| AAU14144 | EAG93220 | YP_160917 |
| AAV74394 | EAH04927 | YP_160918 |
| AAW23162 | EAH08972 | YP_162605 |
| AAW88382 | EAH10377 | YP_172741 |
| AAX54906 | EAH22151 | YP_172822 |
| AAX92679 | EAH31461 | YP_187369 |
| ABB52071 | EAH50033 | YP_192648 |
| ABB52072 | EAH64480 | YP_291268 |
| ABB52073 | EAH79040 | YP_291882 |
| ABB72443 | EAH99976 | YP_376736 |
| AC2035 | EAI02786 | YP_382237 |
| BAB18514 | EAI02787 | YP_397130 |
| BAB79604 | EAI03575 | YP_397570 |
| BAD02742 | EAI05900 | YP_401079 |
| BAD02766 | EAI47456 | ZP_000044 |
| BAD02770 | EAI61004 | ZP_001091 |
| BAD02774 | EAI70669 | ZP_001591 |
| BAD07277 | EAI83938 | ZP_001657 |
| BAD07278 | EAJ05110 | ZP_001690 |
| BAD07285 | EAJ05569 | ZP_001746 |
| BAD07286 | EAJ08876 | ZP_001837 |
| BAD07293 | EAJ35156 | ZP_001867 |
| BAD62106 | EAJ38900 | ZP_002096 |
| BAD62107 | EAJ49645 | ZP_002248 |
| BAE43514 | EAJ54357 | ZP_002450 |
| BAE43517 | EAJ60475 | ZP_002680 |
| BAE43519 | EAJ62838 | ZP_002710 |
| BAE43522 | EAJ62839 | ZP_002791 |
| BAE43526 | EAJ64125 | ZP_002892 |
| BAE43527 | EAJ67499 | ZP_002916 |
| BAE43528 | EAJ76471 | ZP_003036 |
| BAE43533 | EAJ76950 | ZP_003269 |
| BAE43534 | EAJ78637 | ZP_003351 |
| BAE43535 | EAJ78787 | ZP_003487 |
| BAE43537 | EAJ79616 | ZP_003501 |
| BAE43538 | EAJ80356 | ZP_003591 |
| BAE43540 | EAJ81914 | ZP_003628 |
| BAE43541 | EAJ87417 | ZP_00395518 |
| BAE43542 | EAK08514 | ZP_01005155 |
| BAE43543 | EAK08523 | ZP_01005551 |
| BAE43544 | EAK12901 | ZP_01084969 |
| BAE43545 | EAK17149 | ZP_01124481 |
| BAE43546 | EAK22047 | |
| BAE43547 | EAK22180 | |

In another aspect, the DNA construct further includes (c) a promoter, (d) a terminator or stop sequence, (e) a gene that confers resistance to an antibiotic (a "selective marker"), (f) a reporter protein, or a combination thereof.

In one aspect, a regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is a promoter. The term "promoter" refers to a DNA sequence capable of controlling the expression of a coding sequence. In one aspect, the coding sequence to be controlled is located 3' to the promoter. In another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example in response to the presence or absence of a particular metabolite (e.g., lactose or tryptophan), a metal ion, a molecule secreted by a pathogen, or the like. A promoter may also be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: DXP promoter, T3 promoter, T7 promoter, Fe promoter, and GAL1 promoter. Variants of these promoters are also contemplated. The skilled artisan will be able to use site-directed mutagenesis and/or other mutagenesis techniques to modify the promoters to promote more efficient function. The promoter may be positioned, for example, from 10-100 nucleotides away from a ribosomal binding site. In another aspect, the promoter is positioned before the gene that expresses beta-carotene hydroxylase, the gene that expresses lycopene epsilon cyclase, the gene that expresses 1-deoxy-D-xylylose phosphate synthase, or any combination thereof.

In one aspect, the promoter is a GAL1 promoter. In another aspect, the GAL1 promoter is native to the plasmid used to create the vector. In another aspect, a GAL1 promoter is positioned before the gene that expresses beta-carotene hydroxylase, the gene that expresses lycopene epsilon cyclase, and the gene that expresses 1-deoxy-D-xylylose phosphate synthase. In another aspect, the promoter is a GAL1 promoter obtained from or native to the pYES2 plasmid.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an "intrinsic terminator" is a sequence wherein a hairpin structure can form in the nascent transcript and wherein the hairpin disrupts the mRNA/DNA/RNA polymerase complex. As used herein, a "Rho-dependent" transcription terminator requires a Rho factor protein complex to disrupt the mRNA/DNA/RNA polymerase complex.

In another aspect, the terminator in the DNA construct is a CYC1 terminator. In a further aspect, the CYC1 terminator is native to the plasmid used to create the vector.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

In certain aspects, the DNA construct can include a gene that expresses a reporter protein. The selection of the reporter protein can vary. For example, the reporter protein can be a yellow fluorescent protein, a red fluorescent protein, a green fluorescent protein, or a cyan fluorescent protein. In one aspect, the gene that expresses the reporter protein has SEQ ID NO. 4 or a sequence having at least 70%, at least 80%, at least 90% homology, or at least 95% homology therewith. The amount of fluorescence that is produced by the biological device can be detected and quantified using techniques known in the art. For example, spectrofluorometers are typically used to measure fluorescence.

In one aspect, the DNA construct includes the following components from 5' to 3' in the following order: a gene that expresses lycopene epsilon-cyclase, a gene that expresses beta-carotene hydroxylase, and a gene that expresses 1-deoxy-D-xylulose phosphate synthase.

In another aspect, the DNA construct includes the DNA construct comprises the following components from 5' to 3' in the following order: a gene that expresses lycopene epsilon-cyclase having SEQ ID NO. 3 or at least 90% homology thereof, a gene that expresses beta-carotene hydroxylase having SEQ ID NO. 2 or at least 90% homology thereof, and a gene that expresses 1-deoxy-D-xylulose phosphate synthase having SEQ ID NO. 3 or at least 90% homology thereof.

In another aspect, the DNA construct includes the DNA construct comprises the following components from 5' to 3' in the following order: a GAL1 promoter, a gene that expresses lycopene epsilon-cyclase, a CYC1 terminator, a GAL1 promoter, a gene that expresses beta-carotene hydroxylase, a CYC1 terminator, a GAL1 promoter; a gene that expresses 1-deoxy-D-xylulose phosphate synthase, and a CYC1 terminator.

In another aspect, the DNA construct includes the DNA construct comprises the following components from 5' to 3' in the following order: a GAL1 promoter, a gene that expresses lycopene epsilon-cyclase having SEQ ID NO. 3 or at least 90% homology thereof, a CYC1 terminator, a GAL1 promoter, a gene that expresses beta-carotene hydroxylase having SEQ ID NO. 2 at least 90% homology thereof, a CYC1 terminator, a GAL1 promoter, a gene that expresses 1-deoxy-D-xylulose phosphate synthase having SEQ ID NO. 1 or at least 90% homology thereof, and a CYC1 terminator.

Figure 2A:
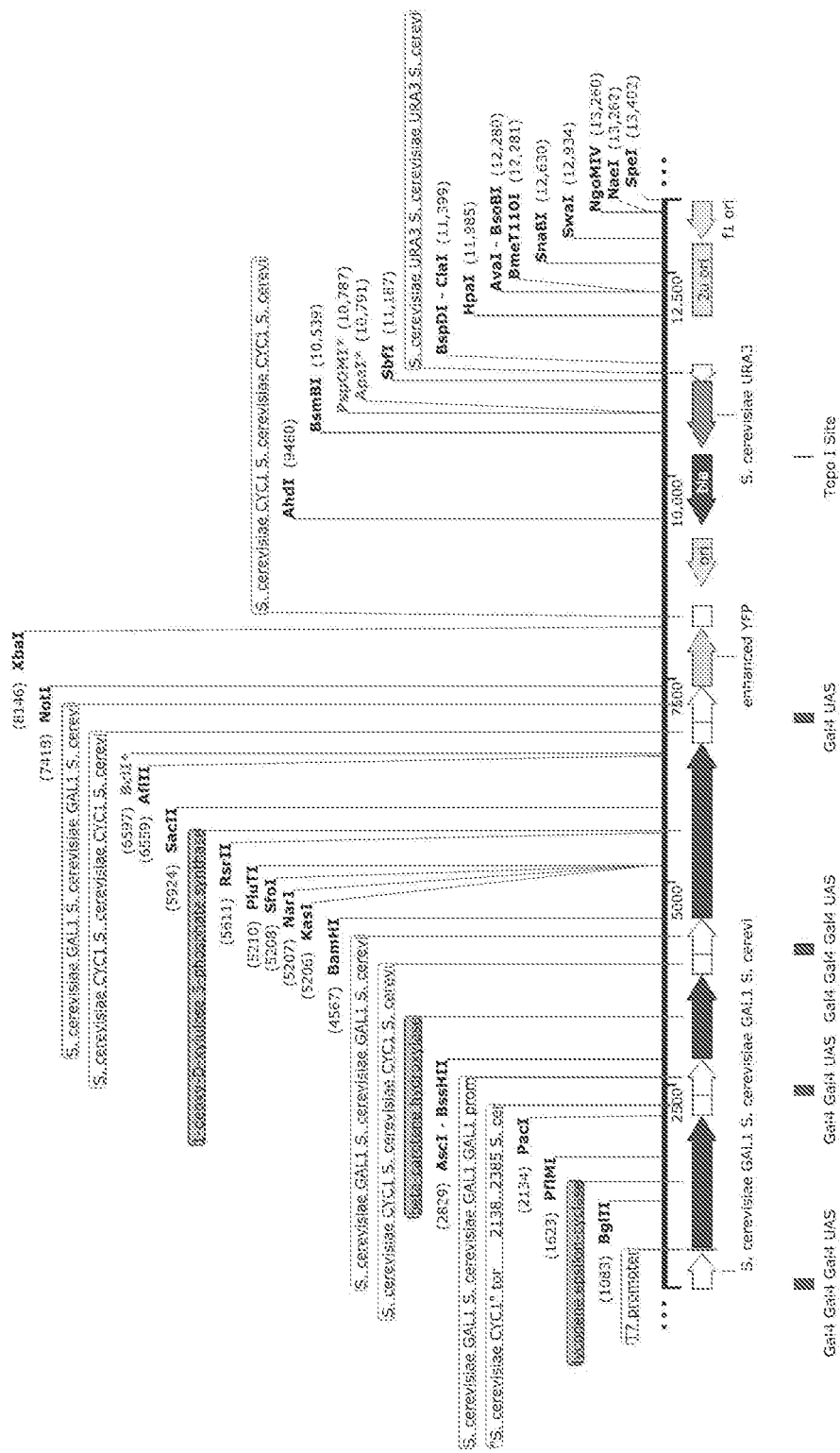
FIGS. 2A and 2B show, respectively, a linear and circular schematic of a constructed pYES2 plasmid showing the direction, placement, and size of genetic parts used of an exemplary DNA device described herein.
Figure 2B:
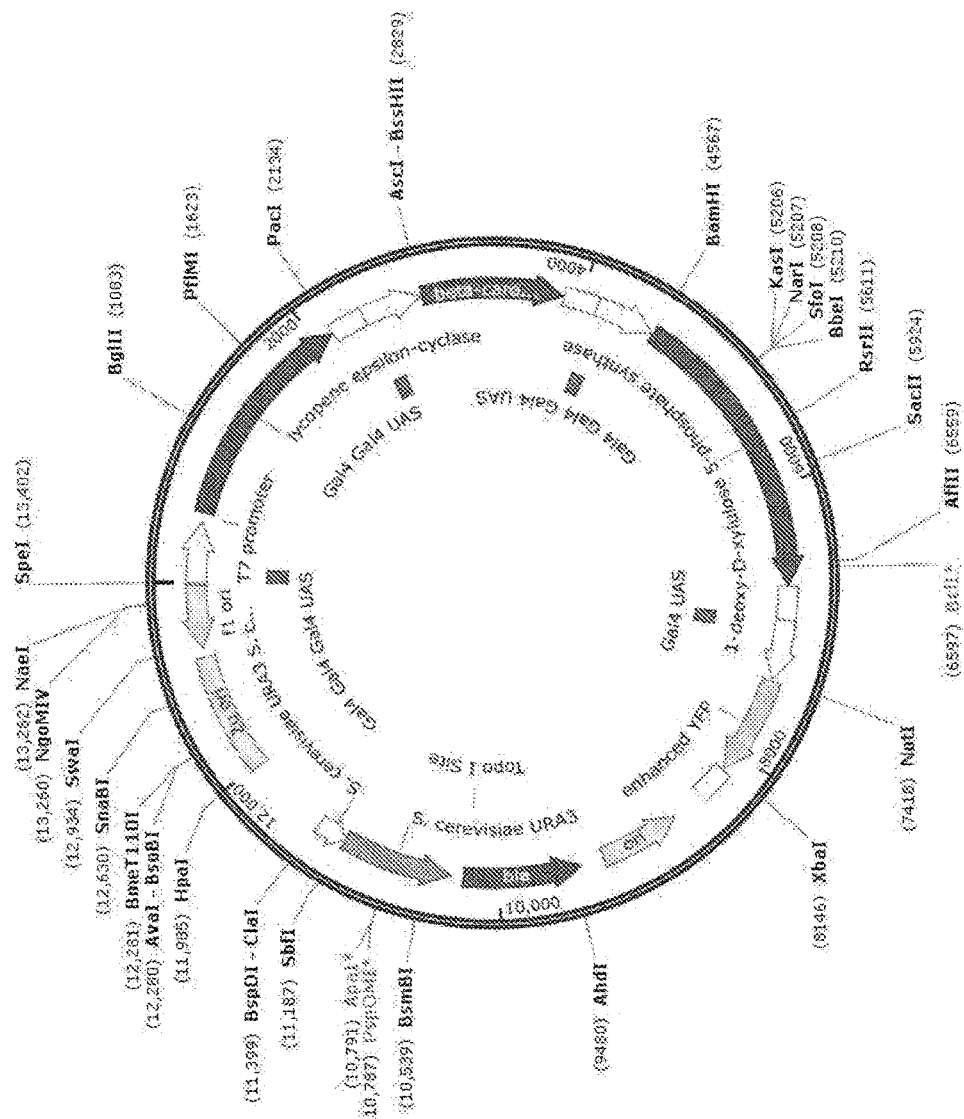

In another aspect the DNA construct is SEQ ID NO. 6. In a further aspect, the DNA construct is the vector depicted in FIGS. 2A and 2B.

In one aspect, the DNA construct includes the following components from 5' to 3' in the following order: a GAL1 promoter, a gene that expresses lycopene epsilon-cyclase, a CYC1 terminator, a GAL1 promoter, a gene that expresses beta-carotene hydroxylase, and a CYC1 terminator.

In another aspect, the DNA construct includes the following components from 5' to 3' in the following order: a GAL1 promoter, a gene that expresses lycopene epsilon-cyclase having SEQ ID NO. 3 or at least 90% homology thereof, a CYC1 terminator, a GAL1 promoter, a gene that expresses beta-carotene hydroxylase having SEQ ID NO. 2 or at least 90% homology thereof, and a CYC1 terminator.

Figure 1B:
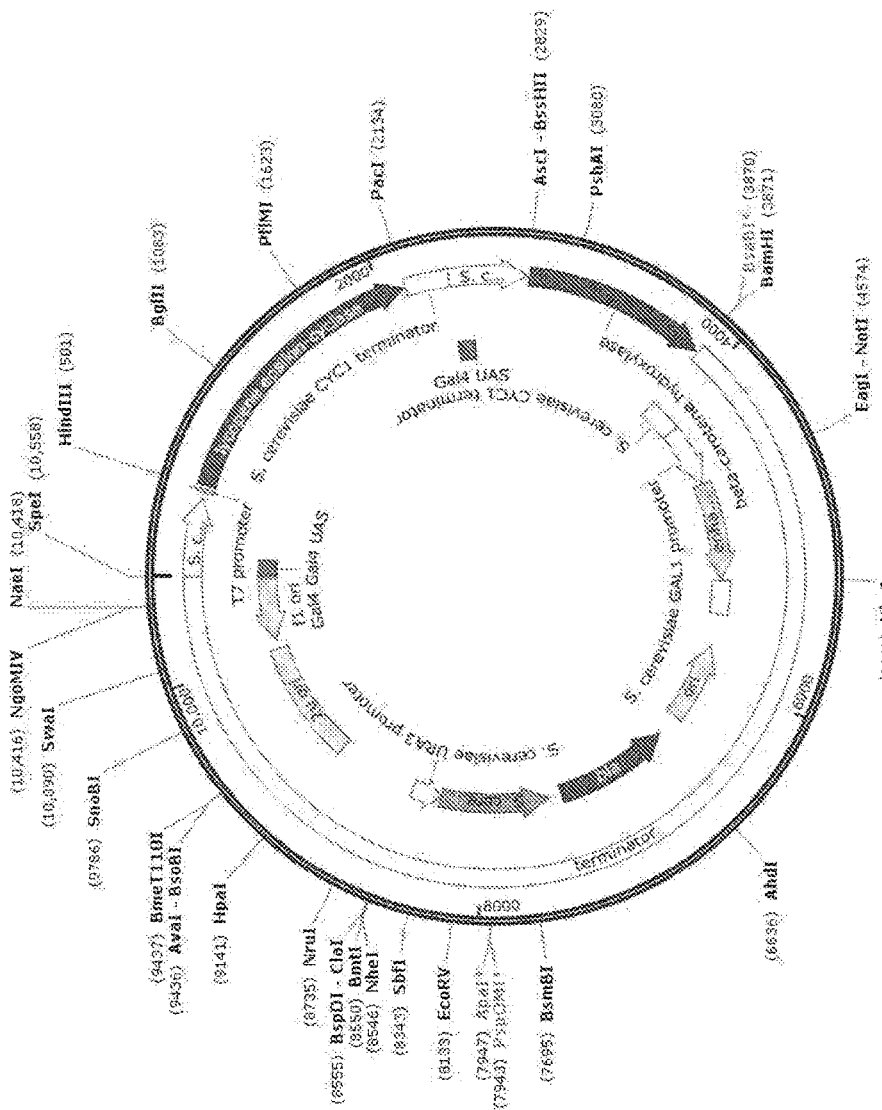

In another aspect the DNA construct is SEQ ID NO. 5. In a further aspect, the DNA construct is the vector depicted in FIGS. 1A and 1B.

The DNA construct described herein can be part of a vector. In one aspect, the vector is a plasmid, a phagemid, a cosmid, a yeast artificial chromosome, a bacterial artificial chromosome, a virus, a phage, or a transposon.

In general, plasmid vectors containing replicon and control sequences that are derived from species compatible with the host cell are used in connection with these hosts. Vectors capable of high levels of expression of recombinant genes and proteins are well known in the art. The vector ordinarily carries a replication origin as well as marking sequences that are capable of providing phenotypic selection in transformed cells. Plasmid vectors useful for the transformation of a variety of host cells are well-known and are commercially available. Such vectors include, but are not limited to, pWLNEO, pSV2CAT, pOG44, pXT1, pSG (Stratagene), pSVK3, pBSK, pBR322, pYES, pYES2, pBSKII, and pUC vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copies per host cell and will contain selectable markers (such as genes for antibiotic resistance) to allow the ordinarily skilled artisan to select host cells that have been successfully transfected with the plasmids (for example, by culturing the host cells in a medium containing the antibiotic).

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector that confers antibiotic resistance can survive. Optionally, only cells containing the vector to be expressed will be cultured, as this will result in the highest production efficiency of the desired gene products (e.g., peptides involved in the synthesis of lycopene). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isoniazid, methicillin, oxacillin, vancomycin, streptomycin, quinolones, rifampin, rifampicin, sulfonamides, cephalothin, erythromycin, streptomycin, gentamycin, penicillin, other commonly-used antibiotics, or a combination thereof.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BasI, NotI, XhoI, SphI, SbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA a distance of from 20 bases to over 1000 bases away from the restriction site. A variety of restriction enzymes are commercially available and their recognition sequences, as well as instructions for use (e.g., amount of DNA needed, precise volumes of reagents, purification techniques, as well as information about salt concentration, pH, optimum temperature, incubation time, and the like) are made available by commercial enzyme suppliers.

In one aspect, a plasmid with a polylinker containing one or more restriction sites can be digested with one restriction enzyme and a nucleotide sequence of interest can be ligated into the plasmid using a commercially available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', often starting just after a promoter, the order and direction of elements inserted into a plasmid are especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleic acid fragments into the plasmid.

In one aspect, the nucleic acids (e.g., genes that express DXP synthase, a carotenoid hydroxylase, and a lycopene cyclase) used in the DNA constructs described herein can be amplified using the polymerase chain reaction (PCR) prior to being ligated into a plasmid or other vector. Typically, PCR-amplification techniques make use of primers or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the ordinarily skilled practitioner with primer design. Primers can optionally incorporate restriction enzyme recognition sites at their 5' ends to assist in later ligation into plasmids or other vectors.

PCR can be carried out using purified DNA, unpurified DNA that has been integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or gene. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the vector can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of the coding sequence.

As used herein, "expression" refers to transcription and/or accumulation of an mRNA derived from a gene or DNA fragment. Expression may also be used to refer to translation of mRNA into a peptide, polypeptide, or protein.

Restriction enzymes and purification techniques known in the art can be used to prepare the DNA constructs. After the vector incorporating the DNA construct has been produced, it can be incorporated into host cells using the methods described below.

II. Biological Devices

In one aspect, a "biological device" is formed when a microbial cell is transfected with the DNA construct described herein. The biological devices are generally composed of microbial host cells, where the host cells are transformed with a DNA construct described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce lycopene or another carotenoid compound.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which exogenous nucleic acid is transferred or introduced into the host cell. A transformed cell includes the primary subject cell and its progeny. The host cells can be naturally-occurring or "recombinant" cells. Recombinant cells are distinguishable from naturally-occurring cells in that naturally-occurring cells do not contain heterologous nucleic acid sequences introduced using molecular biology techniques. In one aspect, the host cell is a prokaryotic cell such as, for example, *Bacillus pumilus* or *E. coli*. In other aspects, the host cell is yeast such as, for example, *Saccharomyces cerevisiae*. Host cells transformed with the DNA construct described herein are referred to as biological devices.

The DNA construct is first delivered into the host cell. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the cell membrane through which the vector containing the DNA construct enters. In certain aspects, two or more types of DNA can be incorporated into the host cells. Thus, different metabolites can be produced from the same plant at enhanced rates.

Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth promoting substances. The addition of peptone provides a readily available source of nitrogen and carbon. A variety of other carbon sources are contemplated, including, but not limited to: monosaccharides such as glucose and fructose, disaccharides such as lactose and sucrose, oligosaccharides, polysaccharides such as starch, and mixtures thereof. Unpurified mixtures extracted from feedstocks are also contemplated and can include molasses, barley malt, and related compounds and compositions. Other glycolytic and tricarboxylic acid cycle intermediates are also contemplated as carbon sources, as are one-carbon substrates such as carbon dioxide and/or methanol in the cases of compatible organisms. The carbon source utilized is limited only by the particular organism being cultured.

Furthermore, the use of different media results in different growth rates and different stationary phase densities. Secondary metabolite production is highest when cells are in stationary phase. A rich media results in a short doubling time and higher cell density at stationary phase. Minimal media results in slow growth and low final cell densities. Efficient agitation and aeration increase final cell densities. A skilled artisan will be able to determine which type of media is best suited to culture a particular species or strain of host cell.

Culturing or fermenting of host cells may be accomplished by any technique known in the art. In one aspect, batch fermentation can be conducted. In batch fermentation, the composition of the culture medium is set at the beginning of culturing and the system is closed to future artificial alterations. In some aspects, a limited form of batch fermentation can be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation can be carried out on any scale and may include methods in which literal "fermentation" is carried out as well as other culture methods that are non-fermentative.

III. Methods for Producing Carotenoids

The biological devices described herein are useful in the production of one or more carotenoids. In one aspect, once the DNA construct has been incorporated into the host cells, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth-promoting substances. For example, the addition of peptone provides a readily-available source of nitrogen and carbon. Furthermore, the use of different types of media results in different growth rates and different stationary phase densities; stationary phase is where secondary metabolite production occurs most frequently. A rich media results in a short doubling time and higher cell density at stationary phase. Minimal media results in slow growth and low final cell densities. Efficient agitation and aeration increase final cell densities.

In one aspect, host cells may be cultured or fermented by any method known in the art. The skilled practitioner will be able to select a culture medium based on the species and/or strain of host cell selected. In certain aspects, the culture medium will contain a carbon source. A variety of carbon sources are contemplated, including, but not limited to: monosaccharides such as glucose and fructose, disaccharides such as lactose or sucrose, oligosaccharides, polysaccharides such as starch, or mixtures thereof. Unpurified mixtures extracted from feedstocks are also contemplated as carbon sources, as are one-carbon substrates such as carbon dioxide and/or methanol in the cases of compatible organisms. The carbon source utilized is limited only by the particular organism being cultured.

Culturing or fermenting of host cells may be accomplished by any technique known in the art. In one aspect, batch fermentation may be conducted. In batch fermentation, the composition of the culture medium is set at the beginning and the system is closed to future artificial alterations. In some aspects, a limited form of batch fermentation may be carried out wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation may be carried out on any scale and may include methods in which literal "fermentation" is carried out as well as other culture methods that are non-fermentative.

In certain aspects, after culturing the biological device to produce the carotenoids(s), the host cells of the device can be lysed with one or more enzymes. For example, when the host cells are yeast, the yeast cells can be lysed with lyticase. In one aspect, the lyticase concentration can be 500, 600, 700, 800, 900, or 1000 µL per liter of culture, where any value can be the lower or upper endpoint of a range (e.g. 500 to 900 µL, 600 to 800 µL, etc.).

In addition to enzymes, other components can be used to facilitate lysis of the host cells. In one aspect, chitosan can be used in combination with an enzyme to lyse the host cells. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation in order to enhance metabolite production. In one aspect, the chitosan is from 60% to about 100%, 70% to 90%, 75% to 85%, or is about 80% acetylated. The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine unit and/or N-acetylglucosamine units. In another aspect, the chitosan includes 5 to 7 glucosamine units and/or N-acetylglucosamine units. In one aspect, the chitosan can be added until a concentration of 0.0015, 0.0025, 0.0050, 0.0075, 0.01, 0.015, 0.02, 0.03, 0.04, or 0.05% (v/v) is achieved in the culture, where any value can be a lower or an upper end-point of a range (e.g., 0.005 to 0.02%, 0.0075 to 0.015%, etc.). Still further in this aspect, the chitosan is present at a concentration of 0.01%.

In a further aspect, the carotenoids(s) can be collected, separated from the microbial cells (lysed or intact), and/or purified through any technique known in the art such as, for example, precipitation, centrifugation, filtration, or the like. The Examples provide an exemplary procedure for producing and purifying the carotenoids(s).

In one aspect, compositions composed of the carotenoids(s) with lysed and/or intact host cells can be used herein where it is not necessary to separate the host cells and other components from the carotenoids(s).

In another aspect, the devices described herein can enhance or increase the production of carotenoids from plant cells where the method involves contacting the plant cells with the biological devices disclosed herein.

The selection of the plant used in the methods described herein can vary depending on the application. For example, a specific plant can be selected that produces certain desirable metabolites. An example of one such metabolite is lycopene. Lycopene has numerous applications in the food industry (e.g., colorants and food enrichment), pharmaceuticals (e.g., anti-cancer agents), and cosmetics (e.g., antioxidants and skin-healing agents). Current techniques for producing lycopene are expensive. For example, lengthy and expensive synthetic procedures are required to produce lycopene on a large scale. The biological devices and methods described herein enhance the production of lycopene from plants that naturally produce lycopene. In one aspect, the plant can include, but is not limited to, lulo or naranjillo (*Solanum quitoense*), tomato (*Solanum lycopersicum*), or carrot (*Daucus carota*).

In another aspect, other carotenoids in addition to lycopene can have the same or similar food, pharmaceutical, and cosmetic applications described above with respect to lycopene.

In one aspect, plant cells when contacted with the biological devices described herein exhibit enhanced production of lycopene and/or other carotenoids. Recipient cell targets include, but are not limited to, meristem cells, Type I, Type II, and Type III callus, immature embryos and gametic cells such as microspores, pollen, sperm, and egg cells. It is contemplated that any cell from which a fertile plant may be regenerated is useful as a recipient cell. Type I, Type II, and Type III callus may be initiated from tissue sources including, but not limited to, immature embryos, immature inflorescences, seedling apical meristems, microspores, and the like. Those cells that are capable of proliferating as callus are also useful herein. Methods for growing plant cells are known in the art (see U.S. Pat. No. 7,919,679). In one aspect, plant calluses grown from 2 to 4 weeks can be used herein. The plant cells can also be derived from plants varying in age. For example, plants that are 80 days to 120 days old after pollination can be used to produce calluses useful herein.

The plant cells can be contacted with the biological device in a number of different ways. In one aspect, the device can be added to media containing the plant cells. In another aspect, the device can be injected into the plant cells via syringe. The amount of device and the duration of exposure to the device can vary as well. In one aspect, the concentration of the device is about $10^3$, $10^4$, $10^5$, $10^6$, $10^7$, $10^8$, or $10^9$ cells/mL of water. In one aspect, when the host cell is a bacterium, the concentration of the device is $10^6$. In another aspect, when the host cell is yeast, the concentration of the device is $10^9$. Different volumes of the biological device can be used as well, ranging from 5 µL to 500 µL.

Once the plant cells have been in contact with the biological device for a sufficient time to produce the metabolite (e.g., carotenoids), the metabolite is isolated. In one aspect, the metabolite is extracted from the media containing the biological device and the plant cells. The selection of the extraction solvent can vary depending upon the solubility of the metabolite.

With current techniques, the extraction of metabolites produced from plants usually requires high initial amounts of plant biomass or material, which in turn requires larger amounts of extraction solvents. The use of higher amounts of extraction solvents adds to the expense of metabolite production. The use of higher amounts of organic solvents also presents environmental risks as well. However, the use of the biological devices described herein produces significantly higher amounts of metabolites such as lycopene and other carotenoids, which means smaller amounts of biomass are required in order to produce and isolate the metabolites when compared with existing techniques. The extraction of plant metabolites using current techniques also requires fresh biomass, which entails agronomic practices, the use of chemicals, and time-consuming extraction methods. Therefore, the use of the biological devices described herein is more cost-effective and safer for the environment than traditional methods for producing and synthesizing carotenoid compounds.

In one aspect, the DNA constructs and vectors described herein are used to treat oleaginous cells to create biological devices. As used herein, the term "oleaginous" refers to a fungus, microbe, or plant cell that can accumulate lipids intracellularly in organelles such as, for example, lipid bodies. In one aspect, lipids can make up from 50% to 75% of the total cellular material, or can be at least 20% of the dry cell weight. In a further aspect, high accumulation of lipids only occurs when the cells are under stress. In a still further aspect, the stress can be any type of stress: heat stress, radiation stress including ultraviolet radiation, salt or other osmotic stress, lack of water, excess water, stress caused by physical damage to a plant (when referring to plant cells), or a combination thereof.

In one aspect, the cells may be naturally oleaginous, as with some strains of oleaginous fungi, or may be genetically modified to create an oleaginous condition. Without wishing to be bound by theory, since carotenoids are generally hydrophobic, it is believed that having a higher concentration of intracellular lipids enables a higher level of carotenoid production and, thus, carotenoid bioaccumulation. In an alternative aspect, having a higher concentration of intracellular lipids may not lead to bioaccumulation of carotenoids, but may allow easier, less expensive methods of carotenoid extraction. In a further aspect, methods of carotenoid extraction from oleaginous cells may require the use of fewer solvents and/or harmful chemicals than traditional methods of carotenoid extraction.

In an alternative aspect, the biological devices are constructed from cells that are not oleaginous and/or do not produce excess oil. In one aspect, the non-oleaginous cells are not modified to produce excess lipids (i.e., the non-oleaginous cells do not possess or comprise any oleaginic modifications). In a further aspect, the non-oleaginous cells contain less than 20% dry cellular weight of lipids. In any of these aspects, a large proportion of lipids and/or lipid bodies in the cell are not required in order to produce and/or accumulate carotenoids. In one aspect, excess carotenoids are excreted from the cells that produce them such as, for example, into a culture medium.

In certain aspects, any of the biological devices described above can be used in combination with a polysaccharide to enhance the production of carotenoids. In one aspect, the plant cells are first contacted with the biological device, then subsequently contacted with the polysaccharide. In another aspect, the plant cells are first contacted with the polysaccharide, then subsequently contacted with the biological device. In a still further aspect, the plant cells are contacted simultaneously with the polysaccharide and the biological device.

In one aspect, the polysaccharide includes chitosan, glucosamine (GlcN), N-acetylglucosamine (NAG), or any combination thereof. Chitosan is generally composed of GlcN and NAG units and can be chemically or enzymatically extracted from chitin, which is a component of arthropod exoskeletons and fungal and microbial cell walls. In certain aspects, the chitosan can be acetylated to a specific degree of acetylation in order to enhance tissue growth during culturing as well as metabolite production. In one aspect, the chitosan is from about 60% to about 100%, 70% to 90%, 75% to 85%, or about 80% acetylated. In one aspect, chitosan isolated from the shells of crab, shrimp, lobster, and/or krill is useful herein.

The molecular weight of the chitosan can vary, as well. For example, the chitosan comprises about 3, 4, 5, 6, 7, 8, 9, 10, 11, 12, 13, 14, 15, 16, 17, 18, 19, or 20 GlcN and/or NAG units. In another aspect, the chitosan includes 5 to 7 GlcN and/or NAG units. In one aspect, the chitosan is in a solution of water and acetic acid at less than 1% by weight, less than 0.75% by weight, less than 0.5% by weight, less than 0.25% by weight, or less than 0.1% by weight. In another aspect, the amount of chitosan that is applied to the plant cells is from 0.1% to 0.01% by weight, from 0.075% to 0.025% by weight, or is about 0.05% by weight. The polysaccharides used herein are generally natural polymers and thus present no environmental concerns. Additionally, the polysaccharide can be used in acceptably low concentrations. In certain aspects, the polysaccharide can be used in combination with one or more growth regulators.

In one aspect, the plant growth regulator is an auxin, a cytokinin, a gibberellin, abscisic acid, or a polyamine. In a further aspect, the auxin is a natural or synthetic auxin. In a still further aspect, the auxin is indole-3-acetic acid (IAA), 4-chloroindole-3-acetic acid (4-Cl-IAA), 2-phenylacetic acid (PAA), indole-3-butyric acid (IBA), 2,4-dichlorophenoxyacetic acid (2,4-D), α-naphthalene acetic acid (α-NAA), 2-methoxy-3,6-dichlorobenzoic acid (dicamba), 4-amino-3,5,6-trichloropicolinic acid (torden or picloram), 2,4,5-trichloropicolinic acid (2,4,5-T), or a combination thereof. In another aspect, the cytokinin is zeatin, kinetin, 6-benzylaminopurine, diphenylurea, thidizuron (TDZ), 6-(γ, γ-dimethylallylamino)purine, or a combination thereof. In another aspect, the gibberellin is gibberellin A1 (GA1), gibberellic acid (GA3), ent-gibberellane, ent-kaurene, or a combination thereof. In yet another aspect, the polyamine is putrescine, spermidine, or a combination thereof.

In one aspect, the plant cell or callus is first contacted with a polysaccharide and subsequently contacted with a plant growth regulator. In another aspect, the plant cell or callus is first contacted with a plant growth regulator and subsequently contacted with a polysaccharide. In an alternative aspect, the plant cell or callus is simultaneously contacted with a polysaccharide and a plant growth regulator. In a further aspect, the plant cell or callus is only contacted with a polysaccharide and is not contacted with a plant growth regulator.

The plant cells can be contacted with the polysaccharide using a number of techniques. In one aspect, the plant cells or reproductive organs (e.g., a plant embryo) can be cultured in agar and medium with a solution of the polysaccharide. In other aspects, the polysaccharide can be applied to a plant callus by techniques such as, for example, coating the callus or injecting the polysaccharide into the callus. In this aspect, the age of the callus can vary depending upon the type of plant. The amount of polysaccharide can vary depending upon, among other things, the selection and number of plant cells. The use of the polysaccharide in the methods described herein permits rapid tissue culturing at room temperature. Due to the ability of the polysaccharide to prevent microbial contamination, the tissue cultures can grow for extended periods of time ranging from days to several weeks. Moreover, tissue culturing with the polysaccharide can occur in the dark and/or light. As discussed above, the plant cells can optionally be contacted with any of the biological devices described above. Thus, the use of the polysaccharides and biological devices described herein is a versatile way to culture and grow plant cells—and, ultimately, plants of interest—with enhanced physiological properties.

In other aspects, the plant cells can be cultured in a liquid medium on a larger scale in a bioreactor. For example, plant cells can be cultured in agar and medium, then subsequently contacted with (e.g., injected) a biological device described herein. After a sufficient culturing time (e.g., two to four weeks), the plant cells are introduced into a container with the same medium used above and, additionally, the polysaccharide. In certain aspects, the polysaccharide can be introduced with anionic polysaccharides including, but not limited to, alginates (e.g., sodium, calcium, potassium, etc.). After the introduction of the polysaccharide, the solution is mixed for a sufficient time to produce a desired result (e.g., production of a desired metabolite).

In one aspect, provided herein is a plant grown by the process of contacting plant gamete cells or a plant reproductive organ with the biological devices disclosed herein. In a further aspect, the plant is produced by the following method:

(a) contacting a plant callus with the biological device;
(b) culturing the plant callus; and
(c) growing the plant from the plant callus.

In one aspect, the plant is lulo or naranjillo (*Solanum quitoense*), tomato (*Solanum lycopersicum*), or carrot (*Daucus carota*). In a further aspect, the method of growing the plant described above includes an additional step (d), wherein the plant callus is cultured with chitosan.

In one aspect, provided herein is a method for producing one or more carotenoids from plant cells, the method including the steps of:

(a) contacting a plant callus of lulo or naranjillo (*Solanum quitoense*), tomato (*Solanum lycopersicum*), or carrot (*Daucus carota*) with a biological device described herein;

(b) culturing the plant callus; and (c) removing the carotenoid from the plant callus.

In an alternative aspect, provided herein is a method for producing one or more carotenoids from fruits, the method including the steps of:

(a) contacting a plant callus of lulo or naranjillo (*Solanum quitoense*), tomato (*Solanum lycopersicum*), or carrot (*Daucus carota*) with a biological device described herein;

(b) culturing the plant callus;

(c) growing a plant from the plant callus, where the plant grows one or more pieces of fruit and;

(d) removing the carotenoid from the fruit.

In an alternative aspect, provided herein is a method for producing one or more carotenoids from leaves, the method including the steps of:

(a) contacting a plant callus of lulo or naranjillo (*Solanum quitoense*), tomato (*Solanum lycopersicum*), or carrot (*Daucus carota*) with a biological device described herein;

(b) culturing the plant callus;

(c) growing a plant from the plant callus, where the plant grows one or more leaves and;

(d) removing the carotenoid from the leaves.

In a further aspect, the same method can be applied to other plant parts including stems, roots, tubers, corms, bulbs, flowers, buds, seeds, and the like. In a still further aspect, the same method can be applied to an entire plant.

In one aspect, the plant callus is immersed in a solution of polysaccharide (e.g., chitosan), then inoculated with the device. In one aspect, the plant callus is that of lulo or naranjillo (*Solanum quitoense*), tomato (*Solanum lycopersicum*), or carrot (*Daucus carota*). The plant callus can be from 2 days up to 20 days old prior to inoculation with the device. The plant callus is then allowed to grow until it is of sufficient weight and size. In one aspect, the plant callus is allowed to grow (i.e., culture) for 1 to 10 weeks after inoculation. The next step involves removal of the lycopene or other carotenoid from the callus. In one aspect, the callus is macerated with a solvent to produce a macerate. The macerate is then extracted with a solvent in order to remove the carotenoid. The extraction solvent is not a harsh solvent, and is generally environmentally friendly. In one aspect, the extraction solvent is ethyl acetate.

In one aspect, lycopene produced from a plant callus can be useful in pharmaceutical applications. Not wishing to be bound by theory, the lycopene produced from the callus will have fewer impurities and thus will be easier to purify for pharmaceutical applications. In another aspect, this is also true for carotenoids other than lycopene produced by the methods described herein. In some aspects, carotenoids such as lycopene may be useful in pharmaceutical and/or nutraceutical applications for the treatment or prevention of diseases such as lung cancer, head and neck cancer, prostate cancer, breast cancer, skin cancer, eye strain or eye diseases; and/or Parkinson's disease. Further in these aspects, the lycopene can be formulated into a pill or capsule; gel or paste; liquid; or powdered medication for oral or topical use, or can be incorporated into a functional food or beverage product. In another aspect, the carotenoids may be incorporated into beauty products including oral supplements, moisturizers, makeup, serums, cleansers, toners, hair care products, lotions, anti-aging preparations, sheet masks, nail care products, and the like for the purpose of improving texture, clarity, and elasticity of the skin, hair, and/or nails. In either of these aspects, the carotenoids may be useful in protecting a subject who consumes or applies them from oxidative stress and oxidative attacks on the immune system.

In another aspect, a plant callus described above can be planted and allowed to grow and mature into a plant bearing fruit and leaves. In one aspect, lycopene or another carotenoid can be isolated from a plant that has been grown from a plant callus inoculated with a device described herein and optionally contacted with a polysaccharide (e.g., chitosan). In one aspect, the carotenoid can be removed from fruit or leaves of a plant grown with the devices described herein. In one aspect, the fruit and leaves of *Solanum quitoense* grown from calluses inoculated with the devices described herein provide a rich source of lycopene.

In one aspect, the fruits and leaves of plants grown with the assistance of the devices described herein can be useful in the production of a number of food products where the food product is enriched with lycopene and other carotenoids. For example, juice from the fruit of *Solanum quitoense* will be enriched with lycopene. Further, the leaves of *Solanum quitoense* can be ground up and consumed as a spice. In either case, the consumer is eating natural products with increased levels of lycopene, which provides health benefits. In yet another aspect, the lycopene produced by the methods described herein can be incorporated in a number of cosmetic and skin care products.

In one aspect, the amount of lycopene or other carotenoid produced by the plant cells, plant callus, and/or plants that have been contacted with the biological device as described herein is from 1.1- to 4-fold greater than the amount of lycopene and/or other carotenoid produced by otherwise identical plant cells, plant callus, and or plants that have not been contacted with the biological device as described herein.

In one aspect, carotenoids can be extracted from callus tissue treated with the devices disclosed herein according to the following procedure:

(a) macerating a sample of callus in ethanol;

(b) adding olive oil and homogenizing;

(c) put the homogenized sample in a separatory funnel and allow to separate;

(d) discard the layer that appears to be a white serum; the other layer is a lycopene-rich solution; and (e) store the carotenoid-rich solution.

The ordinarily-skilled artisan will be able to use established procedures for culturing and providing nutrients to the calluses. In one aspect, calluses ranging in age from one to four weeks, or about 7, 14, 15, 20, 21, 25, or 28 days can be used in the procedures described herein. Further in this aspect, calluses can be inoculated with biological devices and, optionally, chitosan, at the start of carotenoid production. In one aspect, 15-day-old calluses (e.g., 15 days post-inoculation) are used. In a further aspect, the calluses can be placed under an artificial light source in a chamber where conditions such as temperature and humidity are controlled. At various points during callus culture, calluses can be transferred to trays with fresh nutrients or can be directly sprayed with fresh nutrients.

In one aspect, calluses can be grown in trays for a period of time ranging from 1 to 6 months, or can be grown for 1, 2, 3, 4, 5, or 6 months. In one aspect, the calluses are grown for 3 months. Further in this aspect, the calluses have generally sprouted small plants after 3 months of growth.

Several procedures have been established in the art for extraction of lycopene and other carotenoids, or the following procedures can be used. In one aspect, callus samples are lyophilized and weighed. Further in this aspect, the samples are placed in ethyl acetate at a ratio of from 1:50 to 1:200 of callus:ethyl acetate (w:v) and macerated. In one aspect, the ratio is 1:100. In a further aspect, callus samples that have been homogenized can be sealed and placed in a water bath with shaking.

Alternatively, lycopene or another carotenoid can be extracted from fruits. In one aspect, the procedure is the same as with callus, with the exception of the fruit:ethyl acetate (w:v) ratio, which can be from 1:1 to 1:10. In one aspect, the fruit:ethyl acetate ratio is 1:4.

In still another aspect, lycopene or another carotenoid can be extracted from leaves. In a further aspect, the procedure for extracting carotenoids from leaves is the same as for extracting from fruits or calluses, with the exception of the leaf:solvent ratio, which can be from 1:1 to 1:20. In one aspect, the leaf:ethyl acetate ratio is 1:10.

In a further aspect, any solvent in which lycopene or the desired carotenoid can dissolve can be used in place of a portion or all of the ethyl acetate in the procedure described above. In a further aspect, the solvent can be hexane, methanol, acetone, dichloromethane, chloroform, ethanol, diethyl ether, DMSO, toluene, isopropyl alcohol, n-butanol, heptane, acetonitrile, THF, or a combination thereof.

IV. Applications of the Carotenoids

In one aspect, the carotenoids produced by the biological devices described herein have numerous applications. In one aspect, the carotenoids are useful antioxidants in a variety of applications and fields including medical, food, agricultural, nutritional supplements, and surface coatings.

Carotenoids are important in several cell-signaling pathways in plants, including the synthesis of abscisic acid. Abscisic acid is involved in various parts of plant development including growth, seed dormancy, germination and maturation of embryos, cell division, cell and plant elongation, growth of flowers, and responses to stress. In one aspect, the carotenoids produced by the biological devices described herein can be applied to plants, plant cells, plant tissue cultures, plant seeds, fruits, roots, or flowers in order to stimulate the production of abscisic acid.

Carotenoid breakdown products such as ionones, damascenes, and damascenones are found in flowers, tobacco, black tea, and fruits and are commonly used in the fragrance industry. In some aspects, the carotenoids produced by the biological devices disclosed herein can be degraded thermally, chemically, photochemically, or using electromagnetic radiation to produce these breakdown products for use in industry.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions can be used to optimize the product purity and yield obtained from the described process. Only reasonable and routine experimentation will be required to optimize such processes and conditions.

Example 1: Preparation of DNA Construct

The DNA construct was composed of genetic components described herein and assembled in plasmid vectors (e.g., pYES2 and pBSK). Sequences of genes and/or proteins with desired properties were identified in GenBank; these included a DXP synthase gene, a beta-carotene hydroxylase gene, and a lycopene epsilon-cyclase gene. Other genetic parts were also obtained for inclusion in the DNA constructs including, for example, promoter genes (e.g., GAL1 promoter), reporter genes (e.g., yellow fluorescent reporter protein), and terminator sequences (e.g., CYC1 terminator). These genetic parts included restriction sites for ease of insertion into plasmid vectors.

The cloning of the DNA construct into the biological devices was performed as follows. Sequences of individual genes were amplified by polymerase chain reaction using primers that incorporated restriction sites at their 5' ends to facilitate construction of the full sequence to be inserted into the plasmid. Genes were then ligated using standard protocols to form an insert. The plasmid was then digested with restriction enzymes according to directions and using reagents provided by the enzyme's supplier (Promega). The complete insert, containing restriction sites on each end, was then ligated into the plasmid. Successful construction of the insert and ligation of the insert into the plasmid were confirmed by gel electrophoresis.

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis, 1989, *Molecular Cloning: A Laboratory Manual*, $2^{nd}$ ed., Vol. 1, Cold Spring Harbor Laboratory Press: Cold Spring Harbor, N.Y.). Digestion and ligation were used to ensure assembly of DNA synthesized parts using restriction enzymes and reagents (PCR master mix of restriction enzymes: XhoI, KpnI, XbaI, EcoRI, BamHI, and HindIII, with alkaline phosphatase and quick ligation kit, all from Promega). DNA was quantified using a NanoVue spectrophotometer (GE Life Sciences) and a standard UV/Visible spectrophotometer using the ratio of absorbances at 260 nm versus 280 nm. In order to verify final ligations, DNA was visualized and purified via electrophoresis using a Thermo EC-150 power supply.

The DNA construct was made with gene parts fundamental for expression of sequences such as, for example, ribosomal binding sites, native and constitutive promoters, reporter genes, and transcriptional terminators or stops. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. The DNA constructs in FIGS. 1 and 2 were assembled using the techniques above.

After the vector comprising the DNA construct has been produced, the resulting vector can be incorporated into the host cells using the methods known in the art (e.g., Gietz, R. D. and R. H. Schiestl, 2007, *Nature Protocols*, "Quick and easy yeast transformation using the LiAc/SS carrier DNA/PEG method," Vol. 2, 35-37, doi:10.1038/nprot.2007.14).

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein.

Other aspects of the compounds, compositions, and methods described herein will be apparent from consideration of the specification and practice of the compounds, compositions, and methods disclosed herein. It is intended that the specification be considered as exemplary.

What is claimed:

1. A DNA construct comprising the following genetic components: (a) a gene that expresses beta-carotene hydroxylase, (b) a gene that expresses lycopene epsilon cyclase, and (c) a gene that expresses 1-deoxy-D-xylylose phosphate synthase
   wherein the gene that expresses 1-deoxy-D-xylulose phosphate synthase is SEQ ID NO. 1 or a sequence having at least 90% homology thereof.

2. The DNA construct of claim 1, further comprising at least one promoter, wherein the promoter is positioned before the gene that expresses beta-carotene hydroxylase, the gene that expresses lycopene epsilon cyclase, the gene that expresses 1-deoxy-D-xylylose phosphate synthase, or any combination thereof.

3. The DNA construct of claim 1, further comprising at least one promoter positioned before the gene that expresses beta-carotene hydroxylase, the gene that expresses lycopene epsilon cyclase, and the gene that expresses 1-deoxy-D-xylylose phosphate synthase, or any combination thereof.

4. The DNA construct of claim 1, wherein the promoter is a galactokinase (GAL1) promoter.

5. The DNA construct of claim 1, wherein the gene that expresses beta-carotene hydroxylase is SEQ ID NO. 2 or a sequence having at least 90% homology thereof.

6. The DNA construct of claim 1, wherein the gene that expresses lycopene epsilon-cyclase is SEQ ID NO. 3 or a sequence having at least 90% homology thereof.

7. The DNA construct of claim 1, further comprising at least one terminator.

8. The DNA construct of claim 7, wherein the terminator is a cytochrome c-1 (CYC1) terminator.

9. The DNA construct of claim 1, wherein the construct further comprises a gene that confers resistance to an antibiotic.

10. The DNA construct of claim 9, wherein the antibiotic comprises tetracycline, neomycin, kanamycin, ampicillin, hygromycin, chloramphenicol, amphotericin B, bacitracin, carbapenam, cephalosporin, ethambutol, fluoroquinolones, isonizid, methicillin, oxacillin, vancomycin, streptomycin, quinolines, rifampin, rifampicin, sulfonamides, cephalothin, erythromycin, streptomycin, gentamycin, or penicillin.

11. The DNA construct of claim 1, wherein the construct further comprises a gene for expressing a reporter protein.

12. The DNA construct of claim 11, wherein the gene for expressing the reporter protein expresses a fluorescent protein.

13. The DNA construct of claim 11, wherein the reporter protein comprises a red fluorescent protein, a cyan fluorescent protein, a green fluorescent protein, a yellow fluorescent protein, or a combination thereof.

14. The DNA construct of claim 12, wherein the reporter protein is SEQ ID NO. 4 or a sequence having at least 90% homology thereof.

15. The DNA construct of claim 1, wherein the DNA construct comprises the following components from 5' to 3' in the following order: a gene that expresses lycopene epsilon-cyclase, a gene that expresses beta-carotene hydroxylase, and a gene that expresses 1-deoxy-D-xylulose phosphate synthase.

16. The DNA construct of claim 1, wherein the DNA construct comprises the following components from 5' to 3' in the following order: a gene that expresses lycopene epsilon-cyclase is SEQ ID NO. 3 or at least 90% homology thereof, a gene that expresses beta-carotene hydroxylase is SEQ ID NO. 2 or at least 90% homology thereof, and a gene that expresses 1-deoxy-D-xylulose phosphate synthase is SEQ ID NO. 1 or at least 90% homology thereof.

17. The DNA construct of claim 1, wherein the DNA construct comprises the following components from 5' to 3' in the following order: a galactokinase (GAL1) promoter, a gene that expresses lycopene epsilon-cyclase, a cytochrome c-1 (CYC1) terminator, a GAL1 promoter, a gene that expresses beta-carotene hydroxylase, a CYC1 terminator, a GAL1 promoter; a gene that expresses 1-deoxy-D-xylulose phosphate synthase, and a CYC1 terminator.

18. The DNA construct of claim 1, wherein the DNA construct comprises the following components from 5' to 3' in the following order: a galactokinase (GAL1) promoter, a gene that expresses lycopene epsilon-cyclase is SEQ ID NO. 3 or at least 90% homology thereof, a cytochrome c-1 (CYC1) terminator, a GAL1 promoter, a gene that expresses beta-carotene hydroxylase is SEQ ID NO. 2 at least 90% homology thereof, a CYC1 terminator, a GAL1 promoter, a gene that expresses 1-deoxy-D-xylulose phosphate synthase is SEQ ID NO. 1 or at least 90% homology thereof, and a CYC1 terminator.

19. A vector comprising the DNA construct of claim 1.

20. The vector of claim 19, wherein the vector is a plasmid.

21. The vector of claim 19, wherein the vector is pWL-NEO, pSV2CAT, pOG44, pXTI, pSG (Stratagene), pSVK3, pBSK, pBR322, pYES, pYES2, pBSKII, or pUC.

22. A biological device comprising host cells transformed with the DNA construct of claim 1.

23. The biological device of claim 22, wherein the host cells comprise yeast or bacteria.

24. A method for producing a carotenoid, the method comprising growing the biological device of claim 23 for a sufficient time to produce the carotenoid.

25. The method of claim 24, wherein the carotenoid comprises astaxanthin, beta-carotene, canthaxanthin, zeaxanthin, lutein, lycopene, epsilon-carotene, canthaxanthin, antheraxanthin, 7-8-didehydroastaxanthin, alpha-cryptoxanthin, zeta-carotene, diatoxanthin, lactucaxanthin, phytoene, neurosporene, rhodopin, fucoxanthinol, peridinin, siphonaxanthin, neoxanthin, spirilloxanthin, spheroidene, uriolide, uriolide acetate, spheroidenone, rhodopin glucoside, or any combination thereof.

26. A method for producing one or more carotenoids from plant cells, the method comprising contacting the plant cells with the biological device of claim 23.

27. The method of claim 26, wherein the plant cells comprise meristem cells, callus cells, immature embryos, gametic cells, or any combination thereof.

28. The method of claim 26, wherein the plant cells are further contacted with a polysaccharide.

29. The method of claim 28, wherein the polysaccharide comprises chitosan and wherein the chitosan is from 60% to 100% acetylated.

30. The method of claim 29, wherein the chitosan comprises from 3 to 20 glucosamine units, N-acetylglucosamine units, or a combination thereof.

* * * * *

SEQUENCE LISTING

```
<160> NUMBER OF SEQ ID NOS: 6

<210> SEQ ID NO 1
<211> LENGTH: 2160
<212> TYPE: DNA
<213> ORGANISM: Arabidopsis thaliana

<400> SEQUENCE: 1
gccaccatgg cggttgcagg atcgaccatg aacctgcatc tcacttcatc tccatacaag      60
acagttccat cactctgtaa attcaccaga aaacagttcc gattaaaggc ctctgcaacg     120
aatccagacg ctgaagatgg gaagatgatg tttaaaaacg ataaacccaa tttgaaggtc     180
gaattcgctg gggagaaacc ggtgacacca ttactggata ccattaatta ccctgtgcac     240
atgaaaaacc tcaccactca ggatcttgag caattagcag cagaacttag acaagatatt     300
gtatattcag tagcgaatac aggtggtcat ttgagttcaa gtttaggtgt tgttgaattg     360
tctgttgctt tacaccatgt tttcaacacc ccagatgaca agatcatttg ggacgttggt     420
caccaggcat acccacataa gattttgacc ggaagaaggt caaagatgca caccataaga     480
aaaacttctg gtttagctgg tttttcctaaa cgagatgaaa gtgctcatga tgcttttggt     540
gctggacata gttctacaag catctctgct ggactaggta tggctgtcgg tagagattta     600
ttagggaaaa ccaacaacgt gatatcggtg atcggagatg cgccatgac ggccggacga     660 gcatatgagg cgataaataa tgcaggattt cttgattcaa atctaatcgt cgttttaaac     720
gacaacaagc aagtttcatt accgactgcc acgttggacg gacctgcaac tcccgtcggg     780
gctctcagcg gcgctttatc caaattgcaa gccagtacca agttccgtaa gcttcgtgaa     840
gccgccaaga gcattactaa acaaattgga cctcaagcac atgaagtggc ggcgaaagtc     900
gacgaatacg caagaggtat gattagtgct agcgggtcga ctttattcga ggaactcgga     960
ttatactaca tcggtcccgt cgatggtcac aatgttgaag atttagtcaa catttttgaa    1020
aaagtcaagt caatgcccgc acccggaccg gttctaatcc acatcgtgac cgaaaaaggc    1080
aaaggttacc ctcctgctga agccgctgct gaccgtatgc acggagttgt gaagtttgat    1140
gttccaactg gaaaacaatt caagacaaaa tcaccgacac tttcgtatac tcagtatttt    1200
gctgaatcac ttataaaaga agctgaagct gataacaaga ttgtcgcgat acacgccgcc    1260
atgggaggcg gtaccggact caattacttc cagaagaagt gtcctgaacg ttgtttgat    1320 gtcggtatcg cggaacaaca cgcagttact ttcgccgcgg gtttagccac cgaaggtctt    1380
aaaccatttt gcgcgatcta ttcgtcgttt ttgcaacgag gatacgatca agtggtgcat    1440
gacgttgatc tacaaaagtt accggttcgg tttgcgatgg accgagctgg tttagtcggg    1500
gctgatggac cgacacattg tggtgcgttt gacataacct acatggcgtg tctaccaaac    1560
atggtggtga tggctccagc cgatgaagcc gaattgatgc acatggttgc aacggctgca    1620
gccattgacg acagaccgag ttgctttcgg ttcccaagag gcaatggcat tggtgcacca    1680
cttcctccta ataacaaagg gattcccata gaggttggta aggaagaat attacttgaa    1740 ggaactcgtg ttgcgatatt gggatacggt tcgatagttc aagaatgtct aggtgcggct    1800
agcttgcttc aagcccataa cgtgtctgca accgtagccg atgcgcggtt ctgcaaaccg    1860
```

```
ttagacaccg gactgattag acgattagcc aacgagcatg aagtcttact taccgtagag    1920
gaaggctcga ttggtggatt tggatcacac gttgctcact ttctaagctt aaatggtctc    1980
ttagatggaa aacttaagct tagagcaatg actcttcctg ataaatacat tgatcatggt    2040
gcaccacaag atcagcttga agaagccggt ctttcttcaa aacatatttg ttcatctctt    2100
ttatcacttt tgggaaaacc taaagaagca cttcaataca aatcaataat gtaatctaga    2160

<210> SEQ ID NO 2
<211> LENGTH: 1024
<212> TYPE: DNA
<213> ORGANISM: Synechococcus sp. WH 8102

<400> SEQUENCE: 2
atgacccaga gttctgcttt acatcagcaa ccaagaccag tatccacagg ctataggtct      60
gttcccagag agttcgttga tcctcctcct gcatggaatc ccaccgttgc tttgttcttg     120
ggaggatatg gcttagccgc ttttactatt tggggttggt tcttgggtgg tttgcccttta    180 ccagtattat tgtgcactgg attcttggct ttacatttgg aaggtactgt gattcatgac     240
gcatgtcata acgctgctca tcctaatagg tggttaaatc aagccatggg tcatggaagt     300
gctttgttgt taggattctc tttccccgtt ttcactagag tgcacttgga gcatcatgct     360
cacgtcaatg accccaagaa cgacccagat catattgttt caacttttgg cccattgtgg     420
ttaattgccc ctagattctt ttatcacgaa tggttcttct ttcagaggag attatggagg     480
aggtgggaat tgatgcaatg gggattggag agatccgtat ttgtggtcat tgtattatct     540
gcagcaagat ttgagttctt gccattcatt ttcaactgtt ggtttgctcc tgcattgatg     600
gtcggtgtga ctttaggttt gttctttgat tacttgccac ataggccatt tacatcaaga     660
aatagatgga caaatgctag aatatatcct ggtaggttga tgaactggtt gataatgggc     720
caaaattacc acttagttca ccatttatgg ccatcaatac catggtttga atacaaacct     780
gcatatgaag ccacaaagcc attgttagat tctaaaggta gtccacaaag attaggtata     840
ttcgagacaa ggagagatgg ctataacttc ttatacgata tattagttgg tgttagatca     900
cacaagagaa gaagggtaaa aatgagaagg gccgcaaggt tcatgccaat gagatccttc     960
caaagacact ggttaggttt cgtcgataga atcgccatca aaccgaacc tagaagacct    1020 ttaa                                                                 1024

<210> SEQ ID NO 3
<211> LENGTH: 1606
<212> TYPE: DNA
<213> ORGANISM: Zea mays

<400> SEQUENCE: 3
atgggtttga gtggtgccac tatctcagca ccattaggct gctgtgtttt aagatgcggc      60
gctgtgggtg gtgaaaaagc attgaaagct gatgctgaaa ggtggagaag agctggttgg     120
tccagaaggg taggtggtcc aaaagtgaga tgcgtggcaa ccgagaaaca tgatgaaact     180
gcagcagtgg gtgcagctgt tggcgtcgat tttgctgatg aggaagacta tagaaaagga     240
ggtggaggag aattgttgta tgttcagatg caaagtacaa agcctatgga gagtcaatct     300
aagatagctt ctaagttgtc tccaatcagt gatgaaaaca ctgtcttgga cttagttatt     360
ataggatgtg gcccagcagg tttatcattg gcttctgaat cagcaaagaa aggtttgact     420
gttggcttaa tcggtcctga cttgcctttt acaaataact atggtgtttg ggaggatgaa     480
ttcaaagatt tgggtttgga atcctgtatt gaacacgtat ggaaagatac tatagtttat     540
```

```
ttggataata ataagcctat tttgattgga agatcttatg gcagagtaca cagagattta    600
ttacacgagg aattattaaa gagatgttac gaagccggtg tcacatactt aaactctaaa    660
gtggataaga taattgaaag tccagacggc catagagtag tttgttgtga taaaggtagg    720
gaaatcatat gtaggttggc aatcgtcgct tcaggagccg ccagtggtag gttattggaa    780
tacgaggtcg gcggcccag agtttgtgtc cagacagctt atggagtaga ggtagaagtc    840
gagaacaatc cctatgaccc atccttaatg gtctttatgg attacagaga ttgcttcaaa    900
gaagaatttt ctcatacaga acaagaaaac cccactttct tgtatgcaat gcctatgtca    960
ccaaccagag tgttctttga agagacctgc ttagcatcta aagatgcaat gtcatttgat   1020
ttattaaaga aaagattgat gtacagattg aatgctatgg aataaggat attgaaggtg   1080 tatgaagaag aatggagtta catcccagtt ggtggttcat tgcctaacac agaccaaaag   1140
aatttagctt ttggtgctgc tgcaagtatg gttcatcctg ccaccggata ttccgttgtt   1200
aggtccttgt ccgaagcacc taggtacgct tcagtaattt cagacatttt aggtaataga   1260
gttcccgctg aatacatgtt gggaaactcc caaaattact caccatcaat gttagcctgg   1320
aggaccttgt ggccacaaga gagaagagg cagaggtctt tcttcttatt cggattagcc   1380
ttgattattc aattaaacaa tgagggtatt caaactttct tcgaggcctt ctttagagta   1440
ccaagatgga tgtggagagg ttttcttaggt tctacattgt cttctgttga cttgatctta   1500
ttttctttct atatgttcgc cattgcccca aatcagttga gaatgaattt agttagacat   1560
ttgttatctg accctacagg ttcctctatg attaagactt atttaa                 1606
```

<210> SEQ ID NO 4
<211> LENGTH: 890
<212> TYPE: DNA
<213> ORGANISM: Artificial Sequence
<220> FEATURE:
<223> OTHER INFORMATION: Synthetic Construct

<400> SEQUENCE: 4

```
ggattcaaag aggagaaata ctagatggtg agcaagggcg aggagctgtt caccggggtg     60
gtgcccatcc tggtcgagct ggacggcgac gtaaacggcc acaagttcag cgtgtccggc    120
gagggcgagg gcgatgccac ctacggcaag ctgaccctga agttcatctg caccaccggc    180
aagctgcccg tgccctggcc caccctcgtg accaccttcg gctacggcct gcaatgcttc    240
gcccgctacc ccgaccacat gaagctgcac gacttcttca gtccgccat gcccgaaggc    300 tacgtccagg agcgcaccat cttcttcaag gacgacggca actacaagac ccgcgccgag    360
gtgaagttcg agggcgacac cctggtgaac cgcatcgagc tgaagggcat cgacttcaag    420
gaggacggca acatcctggg gcacaagctg gagtacaact acaacagcca caacgtctat    480
atcatggccg acaagcagaa gaacggcatc aaggtgaact tcaagatccg ccacaacatc    540
gaggacggca gcgtgcagct cgccgaccac taccagcaga caccccccat cggcgacggc    600
cccgtgctgc tgcccgacaa ccactacctg agctaccagt ccgccctgag caaagacccc    660
aacgagaagc gcgatcacat ggtcctgctg gagttcgtga ccgccgccgg gatcactctc    720
ggcatggacg agctgtacaa gtaataatac tagagccagg catcaaataa acgaaaggc    780 tcagtcgaaa gactgggcct ttcgttttat ctgttgtttg tcggtgaacg ctctctacta    840
gagtcacact ggctcacctt cgggtgggcc tttctgcgtt tataaagctt                890
```

<210> SEQ ID NO 5

<211> LENGTH: 10563
<212> TYPE: DNA
<213> ORGANISM: Artificial Sequence
<220> FEATURE:
<223> OTHER INFORMATION: Synthetic Construct

<400> SEQUENCE: 5

| | |
|---|---|
| acggattaga agccgccgag cgggtgacag ccctccgaag gaagactctc ctccgtgcgt | 60 |
| cctcgtcttc accggtcgcg ttcctgaaac gcagatgtgc ctcgcgccgc actgctccga | 120 |
| acaataaaga ttctacaata ctagctttta tggttatgaa gaggaaaaat tggcagtaac | 180 |
| ctggccccac aaaccttcaa atgaacgaat caaattaaca accataggat gataatgcga | 240 |
| ttagtttttt agccttattt ctggggtaat taatcagcga agcgatgatt tttgatctat | 300 |
| taacagatat ataaatgcaa aaactgcata accactttaa ctaatacttt caacattttc | 360 |
| ggtttgtatt acttcttatt caaatgtaat aaaagtatca acaaaaaatt gttaatatac | 420 |
| ctctatactt taacgtcaag gagaaaaaac cccggatcgg actactagca gctgtaatac | 480 |
| gactcactat agggaatatt aagcttccta ggatgggttt gagtggtgcc actatctcag | 540 |
| caccattagg ctgctgtgtt ttaagatgcg gcgctgtggg tggtggaaaa gcattgaaag | 600 |
| ctgatgctga aggtggagaa agagctggtt ggtccagaag ggtaggtggt ccaaaagtga | 660 |
| gatgcgtggc aaccgagaaa catgatgaaa ctgcagcagt gggtgcagct gttggcgtcg | 720 |
| attttgctga tgaggaagac tatagaaaag gaggtggagg agaattgttg tatgttcaga | 780 |
| tgcaaagtac aaagcctatg gagagtcaat ctaagatagc ttctaagttg tctccaatca | 840 |
| gtgatgaaaa cactgtcttg gacttagtta ttataggatg tgcccagca ggtttatcat | 900 |
| tggcttctga atcagcaaag aaaggtttga ctgttggctt aatcggtcct gacttgcctt | 960 |
| ttacaaataa ctatggtgtt tgggaggatg aattcaaaga tttgggtttg gaatcctgta | 1020 |
| ttgaacacgt atggaaagat actatagttt attttggataa taataagcct attttgattg | 1080 |
| gaagatctta tggcagagta cacagagatt tattacacga ggaattatta agagatgtt | 1140 |
| acgaagccgg tgtcacatac ttaaactcta aagtggataa gataattgaa agtccagacg | 1200 |
| gccatagagt agtttgttgt gataaaggta gggaaatcat atgtaggttg gcaatcgtcg | 1260 |
| cttcaggagc cgccagtggt aggttattgg aatacgaggt cggcggcccc agagtttgtg | 1320 |
| tccagacagc ttatggagta gaggtagaag tcgagaacaa tccctatgac ccatccttaa | 1380 |
| tggtctttat ggattacaga gattgcttca agaagaatt ttctcataca gaacaagaaa | 1440 |
| accccacttt cttgtatgca atgcctatgt caccaaccag agtgttcttt gaagagacct | 1500 |
| gcttagcatc taaagatgca atgtcatttg atttattaaa gaaaagattg atgtacagat | 1560 |
| tgaatgctat gggaataagg atattgaagg tgtatgaaga agaatggagt tacatcccag | 1620 |
| ttggtggttc attgcctaac acagaccaaa agaatttagc ttttggtgct gctgcaagta | 1680 |
| tggttcatcc tgccaccgga tattccgttg ttaggtcctt gtccgaagca cctaggtacg | 1740 |
| cttcagtaat ttcagacatt ttaggtaata gagttcccgc tgaatacatg ttgggaaact | 1800 |
| cccaaaatta ctcaccatca atgttagcct ggaggacctt gtggccacaa gagagaaaga | 1860 |
| ggcagaggtc tttcttctta ttcggattag ccttgattat tcaattaaac aatgagggta | 1920 |
| ttcaaacttt cttcgaggcc ttctttagag taccaagatg gatgtggaga ggtttcttag | 1980 |
| gttctacatt gtcttctgtt gacttgatct tattttcttt ctatatgttc gccattgccc | 2040 |
| caaatcagtt gagaatgaat ttagttagac atttgttatc tgaccctaca ggttcctcta | 2100 |
| tgattaagac ttatttaact ttataatgat taattaatca tgtaattagt tatgtcacgc | 2160 |

```
ttacattcac gccctccccc cacatccgct ctaaccgaaa aggaaggagt tagacaacct    2220
gaagtctagg tccctattta ttttttttata gttatgttag tattaagaac gttatttata    2280
tttcaaattt ttctttttttt tctgtacaga cgcgtgtacg catgtaacat tatactgaaa    2340
accttgcttg agaaggtttt gggacgctcg aaggctttaa tttgccggat tagaagccgc    2400
cgagcgggtg acagccctcc gaaggaagac tctcctccgt gcgtcctcgt cttcaccggt    2460
cgcgttcctg aaacgcagat gtgcctcgcg ccgcactgct ccgaacaata aagattctac    2520
aatactagct tttatggtta tgaagaggaa aaattggcag taacctggcc ccacaaacct    2580
tcaaatgaac gaatcaaatt aacaaccata ggatgataat gcgattagtt ttttagcctt    2640
atttctgggg taattaatca gcgaagcgat gattttttgat ctattaacag atatataaat    2700
gcaaaaactg cataaccact ttaactaata cttttcaacat tttcggtttg tattacttct    2760
tattcaaatg taataaaagt atcaacaaaa aattgttaat atacctctat actttaacgt    2820
caaggagggc gcgccaccat gacccagagt tctgctttac atcagcaacc aagaccagta    2880
tccacaggct ataggtctgt tcccagagag ttcgttgatc ctcctcctgc atggaatccc    2940
accgttgctt tgttcttggg aggatatggc ttagccgctt ttactatttg gggttggttc    3000
ttgggtggtt tgcccttacc agtattattg tgcactggat tcttggcttt acatttggaa    3060
ggtactgtga ttcatgacgc atgtcataac gctgctcatc ctaataggtg gttaaatcaa    3120
gccatgggtc atggaagtgc tttgttgtta ggattctctt tccccgtttt cactagagtg    3180
cacttggagc atcatgctca cgtcaatgac cccaagaacg acccagatca tattgtttca    3240
acttttggcc cattgtggtt aattgcccct agattctttt atcacgaatg gttcttcttt    3300
cagaggagat tatggaggag gtgggaattg atgcaatggg gattggagag atccgtattt    3360
gtggtcattg tattatctgc agcaagattt gagttcttgc cattcatttt caactgttgg    3420
tttgctcctg cattgatggt cggtgtgact ttaggtttgt tctttgatta cttgccacat    3480
aggccattta catcaagaaa tagatggaca aatgctagaa tatatcctgg taggttgatg    3540
aactggttga taatgggcca aaattaccac ttagttcacc atttatggcc atcaatacca    3600
tggtttgaat acaaacctgc atatgaagcc acaaagccat tgttagattc taaaggtagt    3660
ccacaaagat taggtatatt cgagacaagg agagatggct ataacttctt atacgatata    3720
ttagttggtg ttagatcaca caagagaaga aggggtaaaa tgagaagggc cgcaaggttc    3780
atgccaatga gatccttcca aagacactgg ttaggtttcg tcgatagaat cgccatcaaa    3840
accgaaccta gaagacctttt aaagagataa ggatccgaat tctcatgtaa ttagttatgt    3900
cacgcttaca ttcacgcccct ccccccacat ccgctctaac cgaaaaggaa ggagttagac    3960
aacctgaagt ctaggtccct atttatttt ttatagttat gttagtatta agaacgttat    4020
ttatatttca aattttttctt ttttttctgt acagacgcgt gtacgcatgt aacattatac    4080
tgaaaacctt gcttgagaag gttttgggac gctcgaaggc tttaatttgc cggattagaa    4140
gccgccgagc gggtgacagc cctccgaagg aagactctcc tccgtgcgtc ctcgtcttca    4200
ccggtcgcgt tcctgaaacg cagatgtgcc tcgcgccgca ctgctccgaa caataaagat    4260
tctacaatac tagcttttat ggttatgaag aggaaaaatt ggcagtaacc tggccccaca    4320
aaccttcaaa tgaacgaatc aaattaacaa ccataggatg ataatgcgat tagtttttta    4380
gccttatttc tggggtaatt aatcagcgaa gcgatgattt ttgatctatt aacagatata    4440
taaatgcaaa aactgcataa ccactttaac taatactttc aacattttcg gtttgtatta    4500
```

```
cttcttattc aaatgtaata aaagtatcaa caaaaaattg ttaatatacc tctatacttt    4560
aacgtcaagg aggcggccgc catggtgagc aagggcgagg agctgttcac cggggtggtg    4620
cccatcctgg tcgagctgga cggcgacgta aacggccaca agttcagcgt gtccggcgag    4680
ggcgagggcg atgccaccta cggcaagctg accctgaagt tcatctgcac caccggcaag    4740
ctgcccgtgc cctggcccac cctcgtgacc accttcggct acggcctgca atgcttcgcc    4800
cgctaccccg accacatgaa gctgcacgac ttcttcaagt ccgccatgcc cgaaggctac    4860
gtccaggagc gcaccatctt cttcaaggac gacggcaact acaagacccg cgccgaggtg    4920
aagttcgagg gcgacaccct ggtgaaccgc atcgagctga agggcatcga cttcaaggag    4980
gacggcaaca tcctggggca caagctggag tacaactaca acagccacaa cgtctatatc    5040
atggccgaca gcagaagaa cggcatcaag gtgaacttca agatccgcca caacatcgag    5100
gacggcagcg tgcagctcgc cgaccactac cagcagaaca cccccatcgg cgacggcccc    5160
gtgctgctgc ccgacaacca ctacctgagc taccagtccg ccctgagcaa agaccccaac    5220
gagaagcgcg atcacatggt cctgctggag ttcgtgaccg ccgccgggat cactctcggc    5280
atggacgagc tgtacaagta atctagaggg ccgcatcatg taattagtta tgtcacgctt    5340
acattcacgc cctcccccca catccgctct aaccgaaaag gaaggagtta caacctga    5400 agtctaggtc cctatttatt tttttatagt tatgttagta ttaagaacgt tatttatatt    5460
tcaaattttt ctttttttc tgtacagacg cgtgtacgca tgtaacatta tactgaaaac    5520
cttgcttgag aaggttttgg gacgctcgaa ggctttaatt tgcggccctg cattaatgaa    5580
tcggccaacg cgcggggaga gcggtttgc gtattgggcg ctcttccgct tcctcgctca    5640
ctgactcgct gcgctcggtc gttcggctgc ggcgagcggt atcagctcac tcaaaggcgg    5700
taatacggtt atccacagaa tcaggggata acgcaggaaa gaacatgtga gcaaaaggcc    5760
agcaaaagcc caggaaccgt aaaaaggccg cgttgctggc gttttccat aggctccgcc    5820 cccctgacga gcatcacaaa aatcgacgct caagtcagag gtggcgaaac ccgacaggac    5880
tataaagata ccaggcgttt ccccctggaa gctccctcgt gcgctctcct gttccgaccc    5940
tgccgcttac cggatacctg tccgcctttc tcccttcggg aagcgtggcg ctttctcata    6000
gctcacgctg taggtatctc agttcggtgt aggtcgttcg ctccaagctg gctgtgtgc    6060 acgaaccccc cgttcagccc gaccgctgcg ccttatccgg taactatcgt cttgagtcca    6120
acccggtaag acacgactta tcgccactgg cagcagccac tggtaacagg attagcagag    6180
cgaggtatgt aggcggtgct acagagttct tgaagtggtg gcctaactac ggctacacta    6240
gaaggacagt atttggtatc tgcgctctgc tgaagccagt taccttcgga aaaagagttg    6300
gtagctcttg atccggcaaa caaaccaccg ctggtagcgg tggtttttt gtttgcaagc    6360 agcagattac gcgcagaaaa aaggatctc aagaagatcc tttgatcttt tctacggggt    6420
ctgacgctca gtggaacgaa aactcacgtt aagggatttt ggtcatgaga ttatcaaaaa    6480
ggatcttcac ctagatcctt ttaaattaaa aatgaagttt taaatcaatc taagtatat    6540 atgagtaaac ttggtctgac agttaccaat gcttaatcag tgaggcacct atctcagcga    6600
tctgtctatt tcgttcatcc atagttgcct gactccccgt cgtgtagata actacgatac    6660
gggagcgctt accatctggc cccagtgctg caatgatacc gcgagaccca cgctcaccgg    6720
ctccagattt atcagcaata aaccagccag ccggaagggc cgagcgcaga agtggtcctg    6780
caactttatc cgcctccatc cagtctatta attgttgccg ggaagctaga gtaagtagtt    6840
cgccagttaa tagtttgcgc aacgttgttg gcattgctac aggcatcgtg gtgtcactct    6900
```

```
cgtcgtttgg tatggcttca ttcagctccg gttcccaacg atcaaggcga gttacatgat    6960 ccccccatgtt gtgcaaaaaa gcggttagct ccttcggtcc tccgatcgtt gtcagaagta    7020
agttggccgc agtgttatca ctcatggtta tggcagcact gcataattct cttactgtca    7080
tgccatccgt aagatgcttt tctgtgactg gtgagtactc aaccaagtca ttctgagaat    7140
agtgtatgcg gcgaccgagt tgctcttgcc cggcgtcaat acgggataat agtgtatcac    7200
atagcagaac tttaaaagtg ctcatcattg gaaaacgttc ttcggggcga aaactctcaa    7260
ggatcttacc gctgttgaga tccagttcga tgtaacccac tcgtgcaccc aactgatctt    7320
cagcatcttt tactttcacc agcgtttctg ggtgagcaaa acaggaagg caaaatgccg    7380 caaaaaggg aataagggcg acacggaaat gttgaatact catactcttc cttttcaat    7440 gggtaataac tgatataatt aaattgaagc tctaatttgt gagtttagta tacatgcatt    7500
tacttataat acagtttttt agttttgctg gccgcatctt ctcaaatatg cttcccagcc    7560
tgcttttctg taacgttcac cctctacctt agcatccctt ccctttgcaa atagtcctct    7620
tccaacaata ataatgtcag atcctgtaga gaccacatca tccacggttc tatactgttg    7680
acccaatgcg tctcccttgt catctaaacc cacaccgggt gtcataatca accaatcgta    7740
accttcatct cttccaccca tgtctctttg agcaataaag ccgataacaa atctttgtc    7800 gctcttcgca atgtcaacag tacccttagt atattctcca gtagataggg agcccttgca    7860
tgacaattct gctaacatca aaaggcctct aggttccttt gttacttctt ctgccgcctg    7920
cttcaaaccg ctaacaatac ctgggcccac cacaccgtgt gcattcgtaa tgtctgccca    7980
ttctgctatt ctgtatacac ccgcagagta ctgcaatttg actgtattac caatgtcagc    8040
aaattttctg tcttcgaaga gtaaaaaatt gtacttggcg gataatgcct ttagcggctt    8100
aactgtgccc tccatggaaa aatcagtcaa gatatccaca tgtgttttta gtaaacaaat    8160
tttgggacct aatgcttcaa ctaactccag taattccttg gtggtacgaa catccaatga    8220
agcacacaag tttgtttgct tttcgtgcat gatattaaat agcttggcag caacaggact    8280
aggatgagta gcagcacgtt ccttatatgt agctttcgac atgatttatc ttcgtttcct    8340
gcaggttttt gttctgtgca gttgggttaa gaatactggg caatttcatg tttcttcaac    8400
actacatatg cgtatatata ccaatctaag tctgtgctcc ttccttcgtt cttccttctg    8460
ttcggagatt accgaatcaa aaaaatttca agaaaccga atcaaaaaa aagaataaaa    8520 aaaaaatgat gaattgaatt gaaaagctag cttatcgatg ataagctgtc aaagatgaga    8580
attaattcca cggactatag actatactag atactccgtc tactgtacga tacacttccg    8640
ctcaggtcct tgtcctttaa cgaggcctta ccactctttt gttactctat tgatccagct    8700
cagcaaaggc agtgtgatct aagattctat cttcgcgatg tagtaaaact agctagaccg    8760
agaaagagac tagaaatgca aaaggcactt ctacaatggc tgccatcatt attatccgat    8820
gtgacgctgc agcttctcaa tgatattcga atacgctttg aggagataca gcctaatatc    8880
cgacaaactg ttttacagat ttacgatcgt acttgttacc catcattgaa ttttgaacat    8940
ccgaacctgg gagttttccc tgaaacagat agtatatttg aacctgtata ataatatata    9000
gtctagcgct ttacggaaga caatgtatgt atttcggttc ctggagaaac tattgcatct    9060
attgcatagg taatcttgca cgtcgcatcc ccggttcatt ttctgcgttt ccatcttgca    9120
cttcaatagc atatctttgt taacgaagca tctgtgcttc attttgtaga acaaaaatgc    9180
aacgcgagag cgctaatttt tcaaacaaag aatctgagct gcatttttac agaacagaaa    9240
```

```
tgcaacgcga aagcgctatt ttaccaacga agaatctgtg cttcattttt gtaaaacaaa      9300
aatgcaacgc gacgagagcg ctaattttc aaacaaagaa tctgagctgc attttacag       9360 aacagaaatg caacgcgaga gcgctatttt accaacaaag aatctatact tcttttttgt     9420
tctacaaaaa tgcatcccga gagcgctatt tttctaacaa agcatcttag attacttttt     9480
ttctcctttg tgcgctctat aatgcagtct cttgataact ttttgcactg taggtccgtt    9540
aaggttagaa gaaggctact ttggtgtcta ttttctcttc cataaaaaaa gcctgactcc     9600
acttcccgcg tttactgatt actagcgaag ctgcgggtgc attttttcaa gataaaggca    9660
tccccgatta tattctatac cgatgtggat tgcgcatact ttgtgaacag aaagtgatag    9720
cgttgatgat tcttcattgg tcagaaaatt atgaacggtt tcttctattt tgtctctata    9780
tactacgtat aggaaatgtt tacattttcg tattgttttc gattcactct atgaatagtt    9840
cttactacaa ttttttttgtc taaagagtaa tactagagat aaacataaaa aatgtagagg   9900
tcgagtttag atgcaagttc aaggagcgaa aggtggatgg gtaggttata tagggatata    9960
gcacagagat atatagcaaa gagatacttt tgagcaatgt ttgtggaagc ggtattcgca   10020
atgggaagct ccaccccggt tgataatcag aaaagcccca aaaacaggaa gattgtataa   10080
gcaaatattt aaattgtaaa cgttaatatt ttgttaaaat tcgcgttaaa tttttgttaa    10140
atcagctcat tttttaacga atagcccgaa atcggcaaaa tcccttataa atcaaaagaa    10200
tagaccgaga tagggttgag tgttgttcca gtttccaaca agagtccact attaaagaac    10260
gtggactcca acgtcaaagg gcgaaaaagg gtctatcagg gcgatggccc actacgtgaa    10320
ccatcaccct aatcaagttt ttttggggtcg aggtgccgta aagcagtaaa tcggaagggt   10380
aaacggatgc ccccatttag agcttgacgg ggaaagccgg cgaacgtggc gagaaggaa    10440 gggaagaaag cgaaaggagc gggggctagg gcggtgggaa gtgtaggggt cacgctgggc   10500
gtaaccacca cacccgccgc gcttaatggg gcgctacagg gcgcgtgggg atgatccact   10560
agt                                                                 10563
```

<210> SEQ ID NO 6
<211> LENGTH: 13407
<212> TYPE: DNA
<213> ORGANISM: Artificial Sequence
<220> FEATURE:
<223> OTHER INFORMATION: Synthetic Construct

<400> SEQUENCE: 6

```
acggattaga agccgccgag cgggtgacag ccctccgaag gaagactctc ctccgtgcgt       60
cctcgtcttc accggtcgcg ttcctgaaac gcagatgtgc ctcgcgccgc actgctccga      120
acaataaaga ttctacaata ctagctttta tggttatgaa gaggaaaaat tggcagtaac      180
ctggccccac aaaccttcaa atgaacgaat caaattaaca accataggat gataatgcga     240
ttagtttttt agccttattt ctggggtaat taatcagcga agcgatgatt tttgatctat      300
taacagatat ataaatgcaa aaactgcata accactttaa ctaatacttt caacattttc      360
ggtttgtatt acttcttatt caaatgtaat aaaagtatca acaaaaaatt gttaatatac      420
ctctatactt taacgtcaag gagaaaaaac cccggatcgg actactagca gctgtaatac      480
gactcactat agggaatatt aagcttccta ggatgggttt gagtggtgcc actatctcag      540
caccattagg ctgctgtgtt ttaagatgcg gcgctgtggg tggtggaaaa gcattgaaag     600
ctgatgctga aaggtggaga agagctggtt ggtccgaag ggtaggtggt ccaaaagtga      660
gatgcgtggc aaccgagaaa catgatgaaa ctgcagcagt gggtgcagct gttggcgtcg     720
```

```
attttgctga tgaggaagac tatagaaaag gaggtggagg agaattgttg tatgttcaga       780
tgcaaagtac aaagcctatg gagagtcaat ctaagatagc ttctaagttg tctccaatca       840
gtgatgaaaa cactgtcttg gacttagtta ttataggatg tggcccagca ggtttatcat       900
tggcttctga atcagcaaag aaaggtttga ctgttggctt aatcggtcct gacttgcctt       960
ttacaaataa ctatggtgtt tgggaggatg aattcaaaga tttgggtttg gaatcctgta      1020
ttgaacacgt atggaaagat actatagttt atttggataa taataagcct attttgattg      1080
gaagatctta tggcagagta cacagagatt tattcacga ggaattatta aagagatgtt      1140
acgaagccgg tgtcacatac ttaaactcta agtggataa gataattgaa gtccagacg       1200 gccatagagt agtttgttgt gataaaggta gggaaatcat atgtaggttg caatcgtcg       1260 cttcaggagc cgccagtggt aggttattgg aatacgaggt cggcggcccc agagtttgtg      1320
tccagacagc ttatggagta gaggtagaag tcgagaacaa tccctatgac ccatccttaa      1380
tggtctttat ggattacaga gattgcttca agaagaatt ttctcataca gaacaagaaa      1440
accccacttt cttgtatgca atgcctatgt caccaaccag agtgttcttt gaagagacct      1500
gcttagcatc taaagatgca atgtcatttg atttattaaa gaaagattg atgtacagat      1560 tgaatgctat gggaataagg atattgaagg tgtatgaaga agaatggagt tacatcccag      1620
ttggtggttc attgcctaac acagaccaaa agaatttagc ttttggtgct gctgcaagta      1680
tggttcatcc tgccaccgga tattccgttg ttaggtcctt gtccgaagca cctaggtacg      1740
cttcagtaat ttcagacatt ttaggtaata gagttcccgc tgaatacatg ttgggaaact      1800
cccaaaatta ctcaccatca atgttagcct ggaggaccct gtggccacaa gagagaaaga      1860
ggcagaggtc tttcttctta ttcggattag ccttgattat tcaattaaac aatgagggta      1920
ttcaaacttt cttcgaggcc ttctttagag taccaagatg gatgtggaga ggtttcttag      1980
gttctacatt gtcttctgtt gacttgatct tattttcttt ctatatgttc gccattgccc      2040
caaatcagtt gagaatgaat ttagttagac atttgttatc tgaccctaca ggttcctcta      2100
tgattaagac ttatttaact ttataatgat taattaatca tgtaattagt tatgtcacgc      2160
ttacattcac gccctccccc cacatccgct ctaaccgaaa aggaaggagt tagacaacct      2220
gaagtctagg tccctatta ttttttata gttatgttag tattaagaac gttatttata      2280
tttcaaattt ttcttttttt tctgtacaga cgcgtgtacg catgtaacat tatactgaaa      2340
accttgcttg agaaggtttt gggacgctcg aaggctttaa tttgccggat tagaagccgc      2400
cgagcgggtg acagccctcc gaaggaagac tctcctccgt gcgtcctcgt cttcaccggt      2460
cgcgttcctg aaacgcagat gtgcctcgcg ccgcactgct ccgaacaata aagattctac      2520
aatactagct tttatggtta tgaagaggaa aaattggcag taacctggcc ccacaaacct      2580
tcaaatgaac gaatcaaatt aacaaccata ggatgataat gcgattagtt ttttagcctt      2640
atttctgggg taattaatca gcgaagcgat gattttgat ctattaacag atatataaat      2700
gcaaaaactg cataaccact ttaactaata ctttcaacat tttcggtttg tattacttct      2760
tattcaaatg taataaaagt atcaacaaaa aattgttaat atacctctat actttaacgt      2820
caaggagggc gcgccaccat gacccagagt tctgctttac atcagcaacc aagaccagta      2880
tccacaggct ataggtctgt tcccagagag ttcgttgatc ctcctcctgc atggaatccc      2940
accgttgctg tgttcttggg aggatatggc ttagccgctt ttactatttg gggttggttc      3000
ttgggtggtt tgcccttacc agtattattg tgcactggat tcttggcttt acatttggaa      3060
```

```
ggtactgtga ttcatgacgc atgtcataac gctgctcatc ctaataggtg gttaaatcaa    3120
gccatgggtc atggaagtgc tttgttgtta ggattctctt tccccgtttt cactagagtg    3180
cacttggagc atcatgctca cgtcaatgac cccaagaacg acccagatca tattgtttca    3240
acttttggcc cattgtggtt aattgcccct agattctttt atcacgaatg gttcttcttt    3300
cagaggagat tatggaggag gtgggaattg atgcaatggg gattggagag atccgtattt    3360
gtggtcattg tattatctgc agcaagattt gagttcttgc cattcatttt caactgttgg    3420
tttgctcctg cattgatggt cggtgtgact ttaggtttgt tctttgatta cttgccacat    3480
aggccattta catcaagaaa tagatggaca aatgctagaa tatatcctgg taggttgatg    3540
aactggttga taatgggcca aaattaccac ttagttcacc atttatggcc atcaatacca    3600
tggtttgaat acaaacctgc atatgaagcc acaaagccat tgttagattc taaaggtagt    3660
ccacaaagat taggtatatt cgagacaagg agagatggct ataacttctt atacgatata    3720
ttagttggtg ttagatcaca caagagaaga aggggtaaaa tgagaagggc cgcaaggttc    3780
atgccaatga gatccttcca aagacactgg ttaggtttcg tcgatagaat cgccatcaaa    3840
accgaaccta aagaccttt aaagagataa ggtacctcat gtaattagtt atgtcacgct    3900
tacattcacg ccctccccc catccgctc taaccgaaaa ggaaggagtt agacaacctg    3960
aagtctaggt ccctatttat ttttttatag ttatgttagt attaagaacg ttatttatat    4020
ttcaaatttt tcttttttt ctgtacagac gcgtgtacgc atgtaacatt atactgaaaa    4080
ccttgcttga aaggttttg ggacgctcga aggctttaat ttgccggatt agaagccgcc    4140
gagcgggtga cagccctccg aaggaagact ctcctccgtg cgtcctcgtc ttcaccggtc    4200
gcgttcctga aacgcagatg tgcctcgcgc cgcactgctc cgaacaataa agattctaca    4260
atactagctt ttatggttat gaagaggaaa aattggcagt aacctggccc cacaaacctt    4320
caaatgaacg aatcaaatta acaaccatag gatgataatg cgattagttt tttagcctta    4380
tttctggggt aattaatcag cgaagcgatg attttgatc tattaacaga tatataaatg    4440
caaaaactgc ataaccactt taactaatac tttcaacatt ttcggtttgt attacttctt    4500
attcaaatgt aataaaagta tcaacaaaaa attgttaata tacctctata ctttaacgtc    4560
aaggagggat ccatggcggt tgcaggatcg accatgaacc tgcatctcac ttcatctcca    4620
tacaagacag ttccatcact ctgtaaattc accagaaaac agttccgatt aaaggcctct    4680
gcaacgaatc cagacgctga agatgggaag atgatgttta aaaacgataa acccaatttg    4740
aaggtcgaat tcgctgggga gaaaccggtg acaccattac tggataccat taattaccct    4800
gtgcacatga aaaacctcac cactcaggat cttgagcaat tagcagcaga acttagacaa    4860
gatattgtat attcagtagc gaatacaggt ggtcatttga gttcaagttt aggtgttgtt    4920
gaattgtctg ttgctttaca ccatgttttc aacaccccag atgacaagat catttgggac    4980
gttggtcacc aggcataccc acataagatt ttgaccggaa gaaggtcaaa gatgcacacc    5040
ataagaaaaa cttctggttt agctggtttt cctaaacgag atgaaagtgc tcatgatgct    5100
tttggtgctg gacatagttc tacaagcatc tctgctggac taggtatggc tgtcggtaga    5160 gattattag ggaaaaccaa caacgtgata tcggtgatcg gagatggcgc catgacggcc    5220
ggacgagcat atgaggcgat aaataatgca ggatttcttg attcaaatct aatcgtcgtt    5280
ttaaacgaca caagcaagt ttcattaccg actgccacgt tggacggacc tgcaactccc    5340 gtcgggctc tcagcggcgc tttatccaaa ttgcaagcca gtaccaagtt ccgtaagctt    5400
cgtgaagccg ccaagagcat tactaaacaa attggacctc aagcacatga agtggcggcg    5460
```

```
aaagtcgacg aatacgcaag aggtatgatt agtgctagcg ggtcgacttt attcgaggaa   5520
ctcggattat actacatcgg tcccgtcgat ggtcacaatg ttgaagattt agtcaacatt   5580
tttgaaaaag tcaagtcaat gcccgcaccc ggaccggttc taatccacat cgtgaccgaa   5640
aaaggcaaag gttaccctcc tgctgaagcc gctgctgacc gtatgcacgg agttgtgaag   5700
tttgatgttc caactggaaa acaattcaag acaaaatcac cgacactttc gtatactcag   5760
tattttgctg aatcacttat aaagaagct gaagctgata acaagattgt cgcgatacac   5820
gccgccatgg gaggcggtac cggactcaat tacttccaga gaagtgtcc tgaacgttgt   5880 tttgatgtcg gtatcgcgga acaacacgca gttactttcg ccgcgggttt agccaccgaa   5940
ggtcttaaac cattttgcgc gatctattcg tcgttttgc aacgaggata cgatcaagtg   6000
gtgcatgacg ttgatctaca aaagttaccg gttcggtttg cgatggaccg agctggttta   6060
gtcggggctg atggaccgac acattgtggt gcgtttgaca taacctacat ggcgtgtcta   6120
ccaaacatgg tggtgatggc tccagccgat gaagccgaat tgatgcacat ggttgcaacg   6180
gctgcagcca ttgacgacag accgagttgc tttcggttcc caagaggcaa tggcattggt   6240
gcaccacttc ctcctaataa caaagggatt cccatagagg ttggtaaagg aagaatatta   6300
cttgaaggaa ctcgtgttgc gatattggga tacggttcga tagttcaaga atgtctaggt   6360
gcggctagct tgcttcaagc ccataacgtg tctgcaaccg tagccgatgc gcggttctgc   6420
aaaccgttag acaccggact gattagacga ttagccaacg agcatgaagt cttacttacc   6480
gtagaggaag gctcgattgg tggatttgga tcacacgttg ctcactttct aagcttaaat   6540
ggtctcttag atggaaaact taagcttaga gcaatgactc ttcctgataa atacattgat   6600
catggtgcac cacaagatca gcttgaagaa gccggtcttt cttcaaaaca tatttgttca   6660
tctcttttat cacttttggg aaaacctaaa gaagcacttc aatacaaatc aataatgtaa   6720
gaattctcat gtaattagtt atgtcacgct tacattcacg ccctccccc acatccgctc   6780 taaccgaaaa ggaaggagtt agacaacctg aagtctaggt ccctatttat ttttttatag   6840
ttatgttagt attaagaacg ttatttatat ttcaaatttt tctttttttt ctgtacagac   6900
gcgtgtacgc atgtaacatt atactgaaaa ccttgcttga aaggttttg ggacgctcga   6960 aggctttaat ttgccggatt agaagccgcc gagcgggtga cagccctccg aaggaagact   7020
ctcctccgtg cgtcctcgtc ttcaccggtc gcgttcctga aacgcagatg tgcctcgcgc   7080
cgcactgctc cgaacaataa agattctaca atactagctt ttatggttat gaagaggaaa   7140
aattggcagt aacctggccc cacaaacctt caaatgaacg aatcaaatta caaccatag   7200 gatgataatg cgattagttt tttagcctta tttctggggt aattaatcag cgaagcgatg   7260 attttgatc tattaacaga tatataatg caaaaactgc ataaccactt taactaatac   7320
tttcaacatt ttcggtttgt attacttctt attcaaatgt aataaagta tcaacaaaaa   7380 attgttaata tacctctata ctttaacgtc aaggaggcgg ccgccatggt gagcaagggc   7440
gaggagctgt tcaccggggt ggtgcccatc ctggtcgagc tggacggcga cgtaaacggc   7500
cacaagttca gcgtgtccgg cgagggcgag ggcgatgcca cctacggcaa gctgaccctg   7560
aagttcatct gcaccaccgg caagctgccc gtgccctggc ccaccctcgt gaccaccttc   7620
ggctacggcc tgcaatgctt cgcccgctac cccgaccaca tgaagctgca cgacttcttc   7680
aagtccgcca tgcccgaagg ctacgtccag gagcgcacca tcttcttcaa ggacgacggc   7740
aactacaaga cccgcgccga ggtgaagttc gagggcgaca ccctggtgaa ccgcatcgag   7800
```

```
ctgaagggca tcgacttcaa ggaggacggc aacatcctgg ggcacaagct ggagtacaac    7860
tacaacagcc acaacgtcta tatcatggcc gacaagcaga agaacggcat caaggtgaac    7920
ttcaagatcc gccacaacat cgaggacggc agcgtgcagc tcgccgacca ctaccagcag    7980
aacaccccca tcggcgacgg ccccgtgctg ctgcccgaca ccactacct gagctaccag    8040 tccgccctga gcaaagaccc caacgagaag cgcgatcaca tggtcctgct ggagttcgtg    8100
accgccgccg ggatcactct cggcatggac gagctgtaca agtaatctag agggccgcat    8160
catgtaatta gttatgtcac gcttacattc acgccctccc cccacatccg ctctaaccga    8220
aaaggaagga gttagacaac ctgaagtcta ggtccctatt tatttttta tagttatgtt    8280 agtattaaga acgttatta tatttcaaat ttttcttttt tttctgtaca gacgcgtgta    8340
cgcatgtaac attatactga aaaccttgct tgagaaggtt ttgggacgct cgaaggcttt    8400
aatttgcggc cctgcattaa tgaatcggcc aacgcgcggg gagaggcggt ttgcgtattg    8460
ggcgctcttc cgcttcctcg ctcactgact cgctgcgctc ggtcgttcgg ctgcggcgag    8520
cggtatcagc tcactcaaag gcggtaatac ggttatccac agaatcaggg gataacgcag    8580
gaaagaacat gtgagcaaaa ggccagcaaa agcccaggaa ccgtaaaaag gccgcgttgc    8640
tggcgttttt ccataggctc cgcccccctg acgagcatca caaaaatcga cgctcaagtc    8700
agaggtggcg aaacccgaca ggactataaa gataccaggc gtttccccct ggaagctccc    8760
tcgtgcgctc tcctgttccg accctgccgc ttaccggata cctgtccgcc tttctccctt    8820
cgggaagcgt ggcgctttct catagctcac gctgtaggta tctcagttcg gtgtaggtcg    8880
ttcgctccaa gctgggctgt gtgcacgaac cccccgttca gcccgaccgc tgcgccttat    8940
ccggtaacta tcgtcttgag tccaacccgg taagacacga cttatcgcca ctggcagcag    9000
ccactggtaa caggattagc agagcgaggt atgtaggcgg tgctacagag ttcttgaagt    9060
ggtggcctaa ctacggctac actagaagga cagtatttgg tatctgcgct ctgctgaagc    9120
cagttacctt cggaaaaaga gttggtagct cttgatccgg caacaaacc accgctggta    9180 gcggtggttt ttttgtttgc aagcagcaga ttacgcgcag aaaaaaagga tctcaagaag    9240
atcctttgat cttttctacg gggtctgacg ctcagtggaa cgaaaactca cgttaaggga    9300
ttttggtcat gagattatca aaaaggatct tcacctagat ccttttaaat taaaaatgaa    9360
gttttaaatc aatctaaagt atatatgagt aaacttggtc tgacagttac caatgcttaa    9420
tcagtgaggc acctatctca gcgatctgtc tatttcgttc atccatagtt gcctgactcc    9480
ccgtcgtgta gataactacg atacgggagc gcttaccatc tggccccagt gctgcaatga    9540
taccgcgaga cccacgctca ccggctccag atttatcagc aataaaccag ccagccggaa    9600
gggccgagcg cagaagtggt cctgcaactt tatccgcctc catccagtct attaattgtt    9660
gccgggaagc tagagtaagt agttcgccag ttaatagttt gcgcaacgtt gttggcattg    9720
ctacaggcat cgtggtgtca ctctcgtcgt ttggtatggc ttcattcagc tccggttccc    9780
aacgatcaag gcgagttaca tgatccccca tgttgtgcaa aaaagcggtt agctccttcg    9840
gtcctccgat cgttgtcaga agtaagttgg ccgcagtgtt atcactcatg gttatggcag    9900
cactgcataa ttctcttact gtcatgccat ccgtaagatg cttttctgtg actggtgagt    9960
actcaaccaa gtcattctga gaatagtgta tgcggcgacc gagttgctct tgcccggcgt    10020
caatacggga taatagtgta tcacatagca gaactttaaa agtgctcatc attggaaaac    10080
gttcttcggg gcgaaaactc tcaaggatct taccgctgtt gagatccagt tcgatgtaac    10140
ccactcgtgc acccaactga tcttcagcat cttttacttt caccagcgtt tctgggtgag    10200
```

```
caaaaacagg aaggcaaaat gccgcaaaaa agggaataag ggcgacacgg aaatgttgaa   10260
tactcatact cttccttttt caatgggtaa taactgatat aattaaattg aagctctaat   10320
ttgtgagttt agtatacatg catttactta taatacagtt ttttagtttt gctggccgca   10380
tcttctcaaa tatgcttccc agcctgcttt tctgtaacgt tcaccctcta ccttagcatc   10440
ccttcccttt gcaaatagtc ctcttccaac aataataatg tcagatcctg tagagaccac   10500
atcatccacg gttctatact gttgacccaa tgcgtctccc ttgtcatcta aaccacacc    10560 gggtgtcata atcaaccaat cgtaaccttc atctcttcca cccatgtctc tttgagcaat   10620
aaagccgata acaaaatctt tgtcgctctt cgcaatgtca acagtaccct tagtatattc   10680
tccagtagat agggagccct tgcatgacaa ttctgctaac atcaaaaggc ctctaggttc   10740
ctttgttact tcttctgccg cctgcttcaa accgctaaca atacctgggc ccaccacacc   10800
gtgtgcattc gtaatgtctg cccattctgc tattctgtat acacccgcag agtactgcaa   10860
tttgactgta ttaccaatgt cagcaaattt tctgtcttcg aagagtaaaa aattgtactt   10920
ggcggataat gcctttagcg gcttaactgt gccctccatg gaaaaatcag tcaagatatc   10980
cacatgtgtt tttagtaaac aaattttggg acctaatgct tcaactaact ccagtaattc   11040
cttggtggta cgaacatcca atgaagcaca caagtttgtt tgcttttcgt gcatgatatt   11100
aaatagcttg gcagcaacag gactaggatg agtagcagca cgttccttat atgtagcttt   11160
cgacatgatt tatcttcgtt tcctgcaggt ttttgttctg tgcagttggg ttaagaatac   11220
tgggcaattt catgtttctt caacactaca tatgcgtata tataccaatc taagtctgtg   11280
ctccttcctt cgttcttcct tctgttcgga gattaccgaa tcaaaaaaat ttcaaagaaa   11340
ccgaaatcaa aaaaagaat aaaaaaaaaa tgatgaattg aattgaaaag ctagcttatc    11400
gatgataagc tgtcaaagat gagaattaat tccacggact atagactata ctagatactc   11460
cgtctactgt acgatacact tccgctcagg tccttgtcct ttaacgaggc cttaccactc   11520
ttttgttact ctattgatcc agctcagcaa aggcagtgtg atctaagatt ctatcttcgc   11580
gatgtagtaa aactagctag accgagaaag agactagaaa tgcaaaaggc acttctacaa   11640
tggctgccat cattattatc cgatgtgacg ctgcagcttc tcaatgatat tcgaatacgc   11700
tttgaggaga tacagcctaa tatccgacaa actgttttac agatttacga tcgtacttgt   11760
tacccatcat tgaattttga acatccgaac ctgggagttt tccctgaaac agatagtata   11820
tttgaacctg tataataata tatagtctag cgctttacgg aagacaatgt atgtatttcg   11880
gttcctggag aaactattgc atctattgca taggtaatct tgcacgtcgc atccccggtt   11940
cattttctgc gtttccatct tgcacttcaa tagcatatct ttgttaacga agcatctgtg   12000
cttcattttg tagaacaaaa atgcaacgcg agagcgctaa ttttcaaac aaagaatctg     12060 agctgcattt ttacagaaca gaaatgcaac gcgaaagcgc tattttacca acgaagaatc   12120
tgtgcttcat ttttgtaaaa caaaaatgca acgcgacgag agcgctaatt tttcaaacaa   12180
agaatctgag ctgcattttt acagaacaga aatgcaacgc gagagcgcta ttttaccaac   12240
aaagaatcta tacttctttt tgttctaca aaaatgcatc ccgagagcgc tatttttcta    12300
acaaagcatc ttagattact tttttctcc tttgtgcgct ctataatgca gtctcttgat    12360 aacttttgc actgtaggtc cgttaaggtt agaagaaggc tactttggtg tctattttct    12420
cttccataaa aaaagcctga ctccacttcc cgcgtttact gattactagc gaagctgcgg   12480
gtgcattttt tcaagataaa ggcatccccg attatattct ataccgatgt ggattgcgca   12540
```

```
tactttgtga acagaaagtg atagcgttga tgattcttca ttggtcagaa aattatgaac  12600
ggtttcttct attttgtctc tatatactac gtataggaaa tgtttacatt ttcgtattgt  12660
tttcgattca ctctatgaat agttcttact acaattttt tgtctaaaga gtaatactag  12720
agataaacat aaaaaatgta gaggtcgagt ttagatgcaa gttcaaggag cgaaaggtgg  12780
atgggtaggt tatataggga tatagcacag agatatatag caaagagata cttttgagca  12840
atgtttgtgg aagcggtatt cgcaatggga agctccaccc cggttgataa tcagaaaagc  12900
cccaaaaaca ggaagattgt ataagcaaat atttaaattg taaacgttaa tattttgtta  12960
aaattcgcgt taaatttttg ttaaatcagc tcattttta acgaatagcc cgaaatcggc  13020
aaaatccctt ataaatcaaa agaatagacc gagatagggt tgagtgttgt tccagtttcc  13080
aacaagagtc cactattaaa gaacgtggac tccaacgtca aagggcgaaa aagggtctat  13140
cagggcgatg gcccactacg tgaaccatca ccctaatcaa gttttttggg gtcgaggtgc  13200
cgtaaagcag taaatcggaa gggtaaacgg atgcccccat ttagagcttg acggggaaag  13260
ccggcgaacg tggcgagaaa ggaagggaag aaagcgaaag gagcggggc tagggcggtg  13320 ggaagtgtag gggtcacgct gggcgtaacc accacaccg ccgcgcttaa tggggcgcta  13380
cagggcgcgt ggggatgatc cactagt                                     13407
```